United States Patent [19]

Piper et al.

[11] 4,079,056

[45] Mar. 14, 1978

[54] METHOD OF MAKING PTERIDINE COMPOUNDS

[75] Inventors: James R. Piper; John A. Montgomery, both of Birmingham, Ala.

[73] Assignee: The United States of America as represented by the Department of Health, Education and Welfare, Washington, D.C.

[21] Appl. No.: 563,466

[22] Filed: Mar. 31, 1975

[51] Int. Cl.$^2$ .......................................... C07D 475/08
[52] U.S. Cl. .................................................. 260/251.5
[58] Field of Search ..................................... 260/251.5

[56] References Cited

U.S. PATENT DOCUMENTS 3,509,150   4/1970   Sisenwine ........................ 260/251.5

OTHER PUBLICATIONS

Kittila, "Dimethylformamide Chemical Uses", (1967), pp. 81–85.

Primary Examiner—Paul M. Coughlan, Jr.
Attorney, Agent, or Firm—Holman & Stern

[57] ABSTRACT

A method for the preparation of pteridine compounds such as methotrexate is disclosed. 2,4-diamino-6-pteridine-methanol·HBr is reacted with triphenylphosphine dibromide or phosphorus tribromide to form 6-(bromomethyl)-2,4-diamino-pteridine hydrobromide and the bromine atom in the molecule is then replaced with the functional group, N-[4-(methylamino)-benzoyl]-L-glutamic acid in the case of methotrexate and N-(4-aminobenzoyl)-L-glutamic acid in the case of aminopterin.

8 Claims, No Drawings

METHOD OF MAKING PTERIDINE COMPOUNDS

BACKGROUND OF THE INVENTION

This invention relates to the preparation of pteridine compounds.

The folic acid antimetabolites N-[4-[[(2,4-diamino-6-pteridinyl)-methyl]amino]benzoyl]-L-glutamic acid (aminopterin) and N-[4-[[(2,4-diamino-6-pteridinyl)methyl]methylamino]benzoyl]-L-glutamic acid (methotrexate) were synthesized nearly thirty years ago. Although aminopterin has been used as a folic acid antagonist in the treatment of leukemia and remains of interest for use as a rodenticide, it has not become as important in cancer chemotherapy as methotrexate, which has been in extensive clinical use for over 20 years. Methotrexate has become even more prominent in recent years through its use in newly developed clinical procedures involving its administration in massive doses followed by treatment with citrovorum factor. The use of methotrexate in this manner has greatly increased demands for production.

The usefulness of aminopterin and methotrexate as anticancer agents prompted a still-continuing search for structural variants, analogs, or derivatives that afford greater overall effectiveness. Drawbacks and limitations in available processes for preparing compounds structurally related to these antimetabolites by the common feature of the (2,4-diamino-6-pteridinyl)methyl grouping (unsubstituted at the 7-position) have caused many investigators to seek new synthetic approaches. The improvements needed in order to increase the attainable types and numbers of related compounds are greater versatility, percentage yields, and ease of purification of the products.

SUMMARY OF THE INVENTION

It is, therefore, a primary object of the present invention to provide a method of making pteridine compounds which provides a high yield, versatility, and ease of purification of the products.

It is another object of the present invention to provide a method for making methotrexate, aminopterin, and related compounds, which is free of the aforementioned and other such disadvantages.

The method according to the present invention achieves these objects and concomitantly furnishes improved syntheses of aminopterin, methotrexate, and related compounds.

The method of the invention provides for the union of the (2,4-diamino-6-pteridinyl)methyl grouping with diverse side chains. This result is achieved by nucleophilic displacement reactions of 2,4-diamino-6-(bromomethyl)pteridine hydrobromide (I) with amino, hydroxyl, and sulfhydryl functions of amines (aromatic and aliphatic), phenols, and thiophenol under appropriate accessary conditions.

Nearly all previously reported work on compounds conceivably or actually attainable by the use of I has involved the introduction of the (2,4-diamino-6-pteridinyl)methyl grouping at amine functions. Four methods have been used. Each is mentioned briefly below. Comments are given on the general synthetic utility of each of the four methods in comparison with that of the new process. Specific evaluative comparisons are made when possible in terms of methotrexate. Two previously used methods for attachment of the (2,4-diamino-6-pteridinyl) methyl grouping to oxygen are described after the background on amino compounds. Apparently, analogous sulfur compounds have not been reported.

Until recently, synthetic approaches used for the preparation of aminopterin, methotrexate and related compounds were adaptations of a method used for the preparation of N-[4-[[(2-amino-4-hydroxy-6-pteridinyl)-methyl]amino]benzoyl]-L-glutamic acid (folic acid) generally known as the Waller procedure. This procedure involves the reaction, in one mixture, of three separate organic components: a 4,5-diaminopyrimidine, a suitable three-carbon compound, and an aromatic amine. Adaptation of the Waller procedure to prepare methotrexate thus employs 2,4,5,6-tetraaminopyrimidine, 2,3-dibromopropionaldehyde, and N-[(4-(methylamino)benzoyl]-L-glutamic acid. It is our understanding that methotrexate is prepared commercially by this procedure.

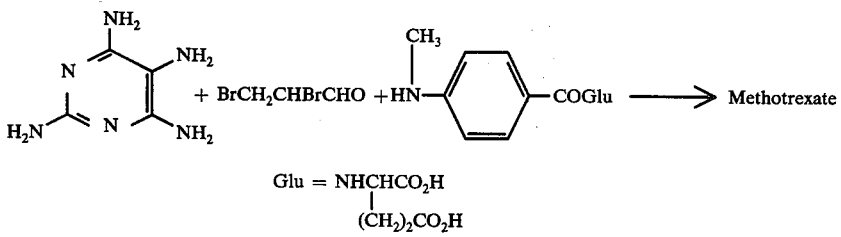

Glu = NHCHCO$_2$H
       |
       (CH$_2$)$_2$CO$_2$H

In view of the complexities of the reaction mixtures, it is not surprising that the Waller procedure gives mixtures of products from which pure desired materials are obtained in low yields following the use of laborious and tedious techniques. Investigators experienced in the use of the Waller procedure have found that, with suitable choices of reaction conditions and purification techniques, yields in the range of 5–10% can be obtained. The previously reported preparation of methotrexate does not give a percentage yield. The preparation of the D-isomer by the Waller procedure was recently reported, with N-[4-(methylamino)benzoyl]-D-glutamic acid being used instead of the L-form, and a column chromatographic (ion-exchange) procedure devised for the purification of methotrexate as obtained commercially was used to advantage to obtain the pure D-form in 6.5% yield. Also in this connection, an elaborate column chromatographic (ion-exchange) method used to separate folic acid analogs has been adapted for use in an assay procedure for commercial methotrexate in order to remove impurities prior to spectrophotometric determination of intact methotrexate. The main contaminant among those removed by these chromatographic methods is N-[4-[[(2-amino-4-hydroxy-6-pteridinyl)methyl]methylamino]benzoyl]-L-glutamic acid (N[10]-methylfolic acid). The application of column techniques would be impractical in large-scale commercial production of methotrexate. A process adaptable to commercial production that would afford methotrexate at acceptable cost, free of $N^{10}$-methylfolic acid, and containing lesser amounts of other impurities as compared to presently available commercial methotrexate would provide obvious advantages. The present process offers those advantages in facile syntheses of methotrexate and various analogs.

A recently developed multistep route in which 2-amino-3-cyano-5-(chloromethyl)pyrazine 1-oxide serves as the key intermediate has been used to prepare the pure diethyl ester of methotrexate and some analogs with altered side chains. The chloromethyl group of the key intermediate in this process affords diversity in the attachment of side chains in the same functional manner as the bromomethyl group of I. An important difference, however, is that the use of I allows direct attachment of the (2,4-diamino-6-pteridinyl)methyl grouping to the side chain while two steps yet remain after the nucleophilic displacement step using 2-amino-3-cyano-5-(chloromethyl)pyrazine 1-oxide. In the sequence leading to methotrexate diethyl ester shown below, removal of the 1-oxide function by treatment with triethyl phosphite was followed by formation of the substituted pteridine ring by condensation of the 2-amino-3-cyanopyrazine system with guanidine.

matographic procedures were used at two points in the process. In contrast, methotrexate itself was obtained in 59% overall yield (for two steps) after hydrolysis in situ of the diethyl ester prepared directly from I and the same side-chain intermediate by the present method.

Earlier studies on new approaches to methotrexate analogs led to a multistep route to 4-[[(2,4-diamino-6-pteridinyl)methyl]methylamino]benzoic acid. This route is potentially applicable to the synthesis of methotrexate, but it is too lengthy (11 steps) to be considered for use in a synthesis otherwise achievable through use of I.

The only other process of which we are aware that has been used to introduce the (2,4-diamino-6-pteridinyl)methyl grouping at amino groups is restricted to the production of secondary amines. It consists of condensation of highly unstable 2,4-diamino-6-pteridinecarboxaldehyde with a primary amine under reducing conditions ($H_2$, $PtO_2$) to produce a secondary amino group at the point of juncture of the two reactants. Concomitant reduction of the 7,8 double bond of the pteridine ring is reversed by oxidation with iodine. This process is, therefore, not applicable to the synthesis of methotrexate or any analog derivable by the procedures mentioned above from a starting compound already bearing a secondary amino group. It has been used to prepare a homolog of aminopterin in a sequence

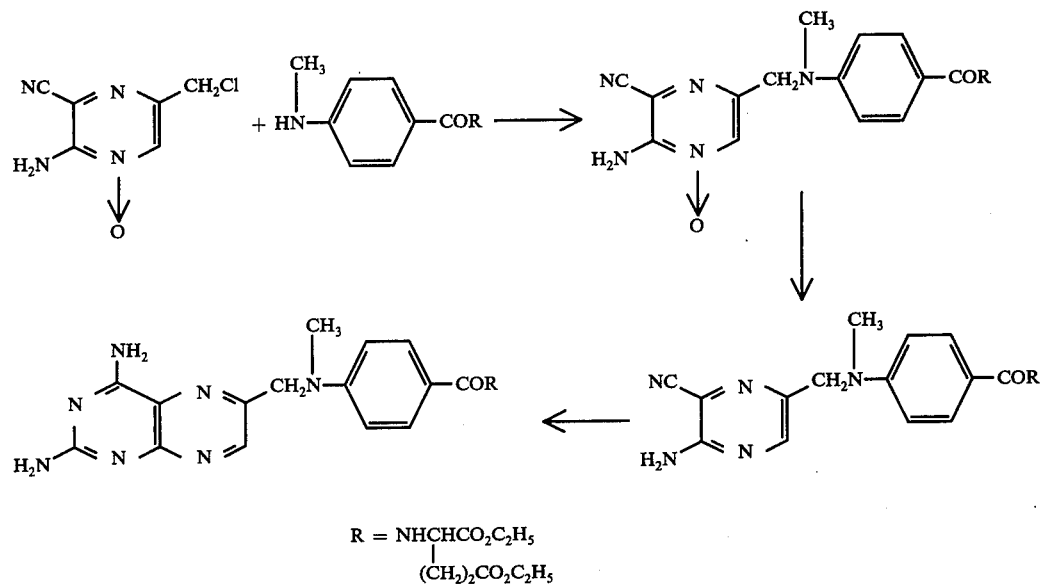

R = NHCHCO$_2$C$_2$H$_5$
       |
       (CH$_2$)$_2$CO$_2$C$_2$H$_5$

The overall yield of pure methotrexate diethyl ester obtained by the above route was calculated from the reported stepwise yields to be 15%, and column chromatographic beginning with the aldehyde and diethyl N-[4-(aminomethyl)benzoyl]-L-glutamate as outlined below.

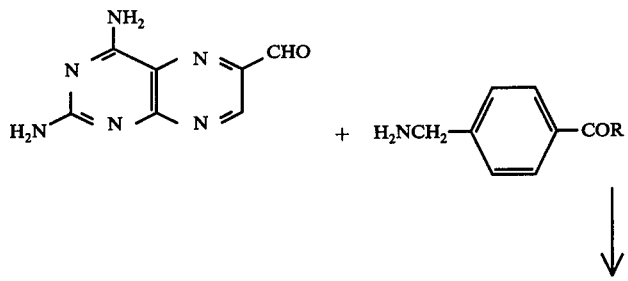

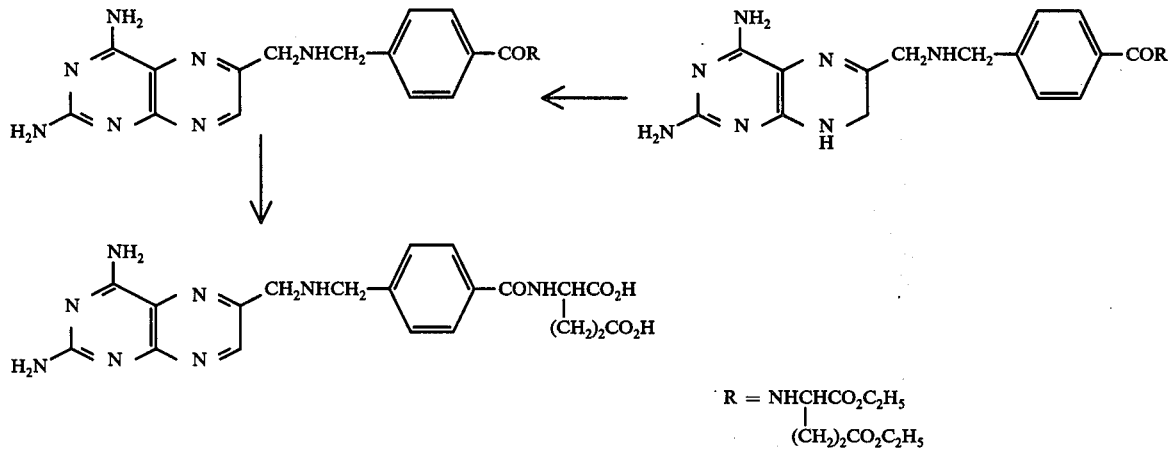

The preparative procedure is scantily described in the published report. Reference is made to the preparation of the corresponding folic acid homolog, which was purified by paper chromatography. The only advantage that this approach appears to offer over that of the present invention is that it affords an umabiguous route to symmetrically substituted hydrazino types where one of the substituents is the (2,4-diamino-6-pteridinyl)-methyl grouping. Obvious disadvantages are (1) the restriction to aminopterin types, (2) the lack of stability of the key intermediate, and (3) the attendant complexities that lead to apparently troublesome purification problems.

Little has been published on aminopterin analogs in which the (2,4-diamino-6-pteridinyl)methyl grouping is attached through oxygen to side chains. The 10-oxa analog of aminopterin, N-[α-(2,4-diamino-6-pteridinyl)-4-anisoyl]-L-glutamic acid, and α-(2,4-diamino-6-pteridinyl)-4-anisic acid shown below were obtained only as crude products following condensation of 2,4,5,6-tetraaminopyrimidine with diethyl N-[4-(3,3-diethoxy-2-oxopropoxy)-benzoyl]-L-glutamate and ethyl 4-(3,3-diethoxy-2-oxopropoxy)benzoate, respectively. A facile preparation of the pure 10-oxa analog of aminopterin through appropriate use of I is described below.

From a method viewpoint, the process mentioned earlier involving the use of 2-amino-3-cyano-5-(chloromethyl)pyrazine 1-oxide could be applied to the synthesis of the 10-oxa analogs shown above. The only related synthesis that has actually been done by that method is that of 2,4-diamino-6-(methoxymethyl)-pteridine.

Before proceeding with a description of the process of the instant invention for making methotrexate, aminopterin, and related compounds, it should be noted that the preparation of I has not heretofore been reported and, therefore, it is still another object of the present invention to provide a process for the production of 6-(bromomethyl)-2,4-diaminopteridine hydrobromide.

According to this aspect of the present invention, 2,4-diamino-6-pteridinemethanol obtained from the condensation of 2,4,5,6-tetraaminopyrimidine and 1,3-dihydroxyacetone according to a reported procedure is converted to its hydrobromide and then treated with triphenylphosphine dibromide or phosphorous tribromide.

Generally, the method of making I and the methotrexate, aminopterin, or other related compounds, follows the following scheme.

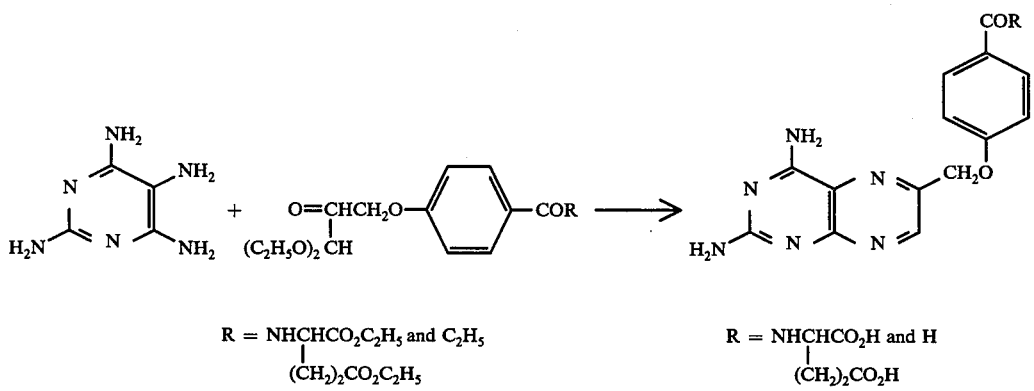

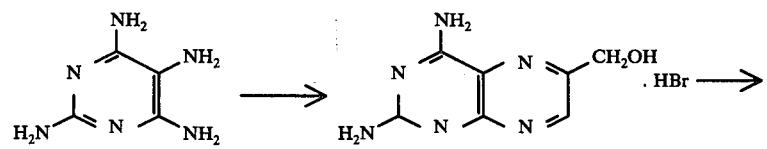

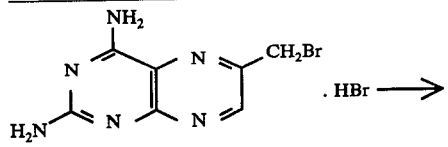

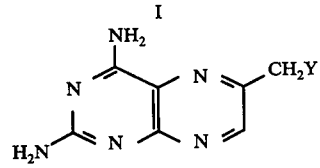

2-31

Designation of Y Groupings in Compounds 2–31

| Compound No. | Y Grouping* |
|---|---|
| 2 | N(CH$_3$)C$_6$H$_4$CONHCH(CO$_2$H)(CH$_2$)$_2$CO$_2$H |
| 3 | NHC$_6$H$_4$CONHCH(CO$_2$H)(CH$_2$)$_2$CO$_2$H |
| 4 | NHC$_6$H$_4$CH$_2$CONHCH(CO$_2$H)(CH$_2$)$_2$CO$_2$H |
| 5 | NHC$_6$H$_4$(CH$_2$)$_2$CONHCH(CO$_2$H)(CH$_2$)$_2$CO$_2$H |
| 6 | NHC$_6$H$_4$SO$_2$NHCH(CO$_2$H)(CH$_2$)$_2$CO$_2$H (as Mg salt) |
| 7 | NH-[pyridine]-CONHCH(CO$_2$H)(CH$_2$)$_2$CO$_2$H |
| 8 | NHC$_6$H$_4$CH$_2$CONHCH(CO$_2$H)CH$_2$CO$_2$H |
| 9 | NHC$_6$H$_4$CONH(CH$_2$)$_3$CO$_2$H |
| 10 | NHC$_6$H$_4$CONHCH$_2$CO$_2$H |
| 11 | N(CH$_3$)C$_6$H$_4$CO$_2$H |
| 12 | NHC$_6$H$_4$CONH$_2$ |
| 13 | NHC$_6$H$_4$CONH(CH$_2$)$_2$CH$_3$ |
| 14 | NHC$_6$H$_4$CON(CH$_3$)$_2$ |
| 15 | NHC$_6$H$_4$COCH$_3$ |
| 16 | NHC$_6$H$_4$NHCOCH$_3$ |
| 17 | NHC$_6$H$_4$(CH$_2$)$_2$NHCOCH$_3$ |
| 18 | NHC$_6$H$_4$OCH$_3$ |
| 19 | NHC$_6$H$_4$Cl |
| 20 | N(CH$_3$)C$_6$H$_5$ |
| 21 | NHC$_6$H$_5$ |
| 22 | N(CH$_3$)(CH$_2$)$_4$CONHCH(CO$_2$CH$_3$)(CH$_2$)$_2$CO$_2$CH$_3$ |
| 23 | N(CH$_3$)(CH$_2$)$_4$CONHCH(CO$_2$H)(CH$_2$)$_2$CO$_2$H |
| 24 | NH(CH$_2$)$_2$C$_6$H$_5$ |
| 25 | NH(CH$_2$)$_3$O(CH$_2$)$_2$OCH$_2$CH$_3$ |
| 26 | NH-[cyclohexyl] |
| 27 | OC$_6$H$_4$CONHCH(CO$_2$C$_2$H$_5$)(CH$_2$)$_2$CO$_2$C$_2$H$_5$ |
| 28 | OC$_6$H$_4$CONHCH(CO$_2$H)(CH$_2$)$_2$CO$_2$H |
| 29 | OC$_6$H$_4$CONH$_2$ |
| 30 | OC$_6$H$_5$ |
| 31 | SC$_6$H$_5$ |

*All disubstituted-benzene types are the 1,4-isomeric forms.

Keeping in mind that the method of making I according to one aspect of the present invention has already been described in general terms, according to the second aspect of the present invention, the method of making pteridine compounds according to the invention may be represented as follows:

The method of making pteridine compounds represented by the formula:

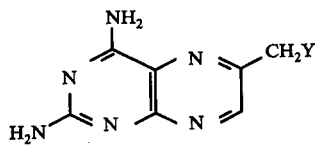

wherein Y is a member selected from the group consisting of —NRR$^1$R$^2$, —NH(CH$_2$)$_2$C$_6$H$_5$,

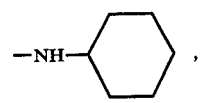

—OR$^3$, and —SC$_6$H$_5$;
R is H or CH$_3$;
R$^1$ is —C$_6$H$_4$R$^4$,

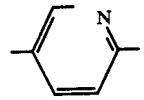

or —(CH$_2$)$_m$—;
R$^2$ is —H, —CONHCH(COOR$^5$)(CH$_2$)$_n$COOR$^5$, —CONHCH$_2$COOH, —COOH, —CONH$_2$, —CONH(CH$_2$)$_2$CH$_3$, —CON(CH$_3$)$_2$, —COCH$_3$, —NHCOCH$_3$, —CONH(CH$_2$)$_3$CO$_2$H, —(CH$_2$)$_2$NHCOCH$_3$, —OCH$_3$, —Cl, or —O(CH$_2$)$_2$OCH$_2$CH$_3$;
R$^3$ is C$_6$H$_4$R$^6$;
R$^4$ is (CH$_2$)$_p$ or (SO$_2$)$_q$;
R$^5$ is —H or —CH$_3$;
R$^6$ is —H, —CONHCH(COOC$_2$H$_5$)(CH$_2$)$_2$COOC$_2$H$_5$, —CONHCH(COOH)(CH$_2$)$_2$COOH, or —CONH$_2$;
m is 2, 3 or 4; n is 1 or 2; p is 0, 1 or 2; and q is 0 or 1 comprising reacting 6-(bromomethyl)-2,4-diaminopteridine hydrobromide with a compound represented by the formula HY, where Y is as defined above, in a reaction medium of N,N-dimethylacetamide or N,N-dimethylformamide and recovering said pteridine compound.

DESCRIPTION OF THE PREFERRED EMBODIMENTS

The starting material, 2,4,5,6-tetraaminopyrimidine was condensed with 1,3-dihydroxyacetone according to the procedure of C. M. Baugh and E. Shaw [*J. Org. Chem.*, 29, 3610 (1964)] as described below. The crude material obtained directly from the reaction mixture was examined by proton magnetic resonance (pmr) spectroscopy in solution in deuteriotrifluoroacetic acid (CF$_3$CO$_2$D) and found to be predominantly the desired 2,4-diamino-6-pteridinemethanol as evidenced by signals at δ5.3 (CH$_2$) and δ9.1 (pteridine position-7). Relatively weak signals near δ2.8 (CH$_3$) and δ8.8 (pteridine ring H) in the spectrum produced by the crude product indicated the presence of one or possibly both of the 6- or 7-methyl-substituted 2,4-diaminopteridines. The hydroxymethyl compound was obtained in nearly pure form after conversion of the mixture of products to hydrobromide salts. The greater solubility of the contaminants in this form in ethanol allowed their nearly complete removal from the hydroxymethyl compound. Pure 2,4-diamino-6-methylpteridine hydrobromide was isolated from an ethanolic filtrate and identified as the 6-methyl isomer by comparisons of its uv-absorption spectra with those of an authentic sample, but no clear evidence was obtained that proved the presence of the 7-methyl isomer. A small percentage of methyl-substituted contaminant that remained in the hydroxymethyl intermediate persisted after the conversion to I (see details below), but was not detectable by pmr spectroscopy or thin-layer chromatography (tlc) in any of the products prepared from I.

The hydroxymethyl compound was converted to I by two procedures. The preferred procedure (Method A) makes use of triphenylphosphine dibromide in N,N-dimethylacetamide (DMAC). In Method B, phosphorus tribromide in N,N-dimethylformamide (DMF) was successfully used, but the yield was much lower than that afforded by Method A.

Samples of I have been stored in refrigerators in tightly sealed containers protected from light for several months without evident deterioration. Gradual darkening has been observed in samples exposed for several weeks to ordinary lighting and ambient conditions in the laboratory.

In all but two of the preparations from I given below, anhydrous DMAC was used as the reaction medium. In the exceptions (6 and 16), which were not tried in DMAC, hexamethylphosphoric triamide was used, probably to no advantage.

In the reaction of I with HY, the ratio of reactants can vary widely, but the preferred molar ratio of I to HY is from 1:1 to 1:4.

Melting points, or approximate decomposition points, are given for some of the compounds described below. They were observed on either a Mel-Temp apparatus or a Kofler Heizbank as indicated in the procedure. In general, these substituted pteridines, particularly those isolated as hydrohalides, lack meaningful melting points. They usually decompose at a high temperature without melting, and the temperature at which decomposition begins is difficult to determine and reproduce. For that reason, melting point determinations were not attempted on all of the compounds prepared. The pmr spectra were determined with a Varian XL-100-15 spectrometer in the solvent indicated ($CF_3CO_2D$ or deuterated dimethyl sulfoxide, $DMSO-d_6$) using tetramethylsilane as internal reference. Chemical shifts quoted for multiplets were measured from the approximate centers, and relative integrals of signal areas are given for the assignment indicated. The uv-absorption spectra were determined with a Cary Model 14 spectrophotometer. Unless indicated otherwise, thin-layer chromatograms on all compounds in which the side chain bears a terminal carboxyl group were run on DEAE-cellulose plates using 0.5 M sodium chloride, 0.2 M in mercaptoethanol, in 0.005 M potassium phosphate buffer at pH 7.0 and were viewed by uv lamps emitting at 254 nm and 365 nm.

EXAMPLE 1

2,4-Diamino-6-pteridinemethanol Hydrobromide 2,4,5,6-Tetraaminopyrimidine.$H_2SO_4$.$H_2O$ (75.0 g, 0.293 mole) was added to a stirred solution of $BaCl_2$.$2H_2O$ (71.5 g, 0.293 mole) in $H_2O$ (1.45 l.) at 85°–90°. The mixture was stirred rapidly at ~90° for 15 min, cooled to 40°, and filtered from $BaSO_4$, which was washed thoroughly on a funnel with $H_2O$. The clear, yellow filtrate was then diluted further with $H_2O$ to give a volume of 4.35 l. This solution of the tetraaminopyrimidine.2HCl was then added to a solution of NaOAc (4.35 l. of 4 N) in which dihydroxyacetone (79.3 g, 0.88 mole) and cysteine.HCl.$H_2O$ (51.5 g, 0.293 mole) had just been dissolved. The resulting solution was stirred mechanically at room temperature while a slow stream of air was continuously passed through it for 26 hr. (Yellow-orange solid began separating after 2 hr.) The mixture was then kept in a refrigerator for 16 hr before the solid was collected, washed successively with cold $H_2O$, EtOH, and $Et_2O$ before it was dried to constant weight in vacuo over $P_2O_5$ at 25°. [The crude product mixture (47 g) was weighed in order to obtain an estimate of the volume of 48% HBr required to form hydrobromide salts.] A mechanically stirred mixture of the dried solid and EtOH (6.05 l.) was heated to 70°, and a solution of 48% HBr (28 ml) in EtOH (490 ml) was added in a thin stream while the mixture was maintained at 70°–75°. The mixture was then refluxed for about 5 min with rapid stirring while nearly all of the solid dissolved. The hot solution was treated with Norit and filtered through a Celite mat. The clear yellow filtrate was kept in a refrigerator overnight while a first crop of orange-colored solid separated. The collected solid was washed with EtOH, then dried in vacuo (56° over $P_2O_5$) to give 17.2 g of product. The filtrate was concentrated by evaporation (rotary evaporator, $H_2O$ aspirator, bath to 35°) to about 2 l. and then refrigerated to give a second crop, which was dried as before, of 10.2 g; total yield 27.4 g (34%). The pmr spectrum of this material in $CF_3CO_2D$ showed it to contain a barely detectable amount of methyl-substituted 2,4-diaminopteridine.HBr as evidenced by very weak signals at $\delta 2.83$ ($CH_3$) and $\delta 8.85$ (pteridine ring H). Strong signals produced by the desired product occur at $\delta 5.28$ (6-$CH_2O$) and $\delta 9.08$ ($C_7$-H). The proportion of desired product to the methyl-substituted contaminant was estimated from the pmr integrals to be 20:1. The pmr spectrum also revealed retention of a small amount of EtOH in the product dried as described but not enough to interfere with the conversion of it to I.

EXAMPLE 1A 2,4-Diamino-6-(bromomethyl)pteridine Hydrobromide (I) Method A

Bromine (59.6 g, 0.373 mole) was added dropwise over a 30-min period to a stirred solution of triphenylphosphine (97.7 g, 0.373 mole) in anhydrous DMAC (486 ml) kept at ~10° (ice bath) and protected from atmospheric moisture. (Bromine remaining in the funnel was rinsed with 10 ml of DMAC). A smooth suspension containing finely divided, crystalline triphenylphosphine dibromide resulted. The 2,4-diamino-6-pteridinemethanol. HBr (25.4 g, 0.093 mole) described above was added in one portion through a powder funnel (with the aid of 10 ml DMAC). The ice bath was removed, and the stirred mixture was allowed to warm to 20°–25°. After about 1 hr, complete solution had occurred. The solution, which gradually developed a dark-red color, was kept at 20°–25° for 1 hr longer and was then chilled (ice bath) before it was treated with EtOH (72 ml). After overnight refrigeration, the solvents were removed by evaporation in vacuo (Swissco evaporator, pressure <1 mm, bath <45°). The dark, semisolid residue was stirred with two 300-ml portions of $C_6H_6$ (to remove triphenylphosphine oxide), and each portion was removed from the $C_6H_6$-insoluble product by decantation. The solid that remained was dissolved with stirring in glacial AcOH (660 ml) which had been preheated to 80°. The mixture was kept in a bath at 80° until solution was complete. Tan crystalline solid separated as the dark solution was allowed to cool. Overnight refrigeration caused the AcOH to partially freeze. When it had thawed, the solid was collected, washed with chilled AcOH followed by $Et_2O$, and dried in vacuo (over $P_2O_5$ and NaOH pellets) at successive temperatures of 25°, 56°, and 110°. (The higher temperature was necessary for complete removal of AcOH). The yield was 15.3 g (49%). (Some runs afforded 60% yield). This sample was further purified by reprecipitation from MeOH solution (Norit) by addition of $Et_2O$ followed by drying in vacuo (25°, $P_2O_5$), yield 13.0 g (42%) of pale-yellow solid. Spectral data: λ max, nm (ε × $10^{-3}$), 0.1 NCl, 249 (17.3), 339 (10.5), 353 (sh); pH 7, 258 (21.2), 370 (6.87); 0.1 N NaOH, 258 (21.5), 370 (6.94); pmr ($CF_3CO_2D$), δ4.70 (s, 2, $CH_2$) and 9.08 (s, 1, $C_7$—H); estimated proportion relative to the methyl-substituted contaminant, 25:1. These spectral properties are in close agreement with those of a similarly obtained sample that gave the following elemental analysis results. Anal. Calcd for $C_7H_7BrN_6 \cdot HBr$: C, 25.02; H, 2.40; Br, 47.56; N, 25.01. Found: C, 25.22; H, 2.44; Br, 47.30; N, 24.99. The 13.0-g sample described above gave the following results. Anal. Found: C, 25.59; H, 2.79; N, 24.62. The preparation of I described above is typical of several runs that gave similar yields of material whose pmr spectra differed only slightly in the estimated proportion of I with respect to the methyl-substituted contaminant. The proportions usually ranged from 16:1 to 25:1, which corresponds to a percentage of I of 94 to 96%. Samples of I of this degree of purity proved to be suitable for use in the preparations of 2-31.

EXAMPLE 1B

(I) Method B

Anhydrous DMF (50 ml) was added in one portion with rapid stirring to freshly distilled $PBr_3$ (5.0 g, 18 mmoles). A mildly exothermic reaction occurred with the temperature of the resulting mixture rising to 35° within 2 min. The stirred mixture was allowed to cool to 28° while a white solid precipitated. 2,4-diamino-6-pteridinemethanol hydrobromide (5.0 g, 18 mmoles) was then added. The temperature of the stirred mixture rose rapidly to 37°, and the solids dissolved. Stirring was continued for 30 min while the temperature returned to 25°. $Et_2O$ (200 ml) was then added with stirring while dark semisolid material separated. The mixture was stirred for 1 hr before the supernatant was removed by decantation. The residue was stirred with more $Et_2O$, which was also removed by decantation, and was then dissolved in AcOH (40 ml). The dark solution was left overnight while crude solid separated. The brown solid was collected, washed successively with AcOH and $Et_2O$, and then dissolved in $CH_3OH$ (40 ml). Norit treatment (for about 3 min) followed by filtration through Celite gave a clear yellow solution, which was diluted with $Et_2O$ to precipitate I as a pale-yellow solid in 16% yield (1.0 g). Examination of this material by tlc (silica gel, 4:1 $CHCl_3$—$CH_3OH$) showed one major spot, which fluoresced under uv light, with an impurity remaining at the origin. A second reprecipitation from Norit-treated $CH_3OH$ solution by addition of $Et_2O$ removed most of the immobile contaminant but lowered the yield to 11% (0.68 g); pmr ($CF_3CO_2D$) δ4.7 (s, 2, $CH_2$), 9.1 (s, 1, $C_7$-H), and a weak spurious signal at δ4.0 ($CH_3CO_2CH_3$, from retained $CH_3OH$ after esterification with the solvent). The proportion of I to $CH_3OH$ of 4:1 estimated from the pmr spectrum is consistent with the results of elemental analysis. Anal. Calcd for $C_7H_7BrN_6 \cdot HBr \cdot 0.25CH_3OH$; C, 25.31; H, 2.64; N, 24.43. Found: C, 25.14; H, 2.84; N, 24.18.

EXAMPLE 2

N-[4-[[(2,4-Diamino-6-pteridinyl)methyl]methylamino]-benzoyl]-L-glutamic acid (2, Methotrexate) Trihydrate A stirred mixture of I (0.34 g, 1.0 mmole) and diethyl N-[4-(methylamino)benzoyl]-L-glutamate (0.37 g, 1.1 mmole) in DMAC (4 ml) was kept at 53°–57° (bath temperature) for 4 hrs. (Solution occurred a few minutes after heating was started.) The dark-orange solution was cooled to room temperature before $H_2O$ (20 ml) and NaOH solution (2 ml of 2 N) were added successively with rapid stirring (no external cooling). The finely divided orange-yellow precipitate that formed dissolved readily with stirring. When solution occurred more $H_2O$ (10 ml) was added. After 16 hrs at room temperature the orange solution was treated with Norit (about 50 mg) and filtered through a Celite mat. The mat was washed with $H_2O$ until the washings were colorless. The combined filtrate and wash solution was treated with sufficient 1 N HCl to lower the pH to 5.5. The turbid mixture was then clarified by treatment with Norit followed by filtration through Celite as before. The filtrate (now approximately 85 ml volume) was treated with 1 N HCl to lower the pH to 4.0 where a voluminous yellow-orange precipitate formed. The mixture was refrigerated for about 2 hrs before the precipitate was collected and dried in vacuo (25°–30°, $P_2O_5$). The dried solid (0.32 g) was dissolved in NaOH solution (20 ml of 0.08 N). After treatment with Norit and filtration as before, the pH was lowered (from 12.1) to 5.5. The faintly turbid mixture was clarified (Norit, Celite) as before, and the clear filtrate was acidified to pH 4.0. After a refrigeration period, the yellow-orange solid was collected, washed with $H_2O$, and dried in vacuo (25°–30°, $P_2O_5$) to give $2 \cdot 3H_2O$ in 59% yield (0.30 g). Anal. Calcd for $C_{20}H_{22}N_8O_5 \cdot 3H_2O$: C, 47.24; H, 5.55; N, 22.04. Found: C, 47.42; H, 5.15; N, 22.05. Spectral data: λmax, nm (ε × $10^{-3}$), 0.1 NCl, 243 (18.9), 307 (22.4); pH 7, 257 (24.8), 302 (25.1), 370 (7.90); 0.1 N NaOH, 257 (25.6), 302 (25.1), 370 (8.14); pmr (DMSO-$d_6$), δ 2.05 (m, 2, $CHCH_2CH_2$), 2.30 (m, 2, $CH_2CO_2H$), 3.20 (s, 3, $CH_3$), 4.38 (m, 1, $NHCHCO_2H$), 4.82 (s, 2, $CH_2N$), 6.85 and 7.73 (m, 4, $C_6H_4$), 7.05 (broad s, 2, $NH_2$), 7.9 (very broad s, 2, $NH_2$), 8.20 (d, 1, NHCO), 8.62 (s, 1, $C_7$—H); ir, identical with that of an authentic sample. A thin-layer chromatogram revealed one uv-absorbing spot (identical with that produced by authentic 2) with a very faint fluorescent spot at or near the origin. The appearance of this chromatogram agrees with the published description of that produced by the D-form of 2 prepared by the Waller procedure and purified by a method that included ion-exchange column chromatography.

The results of an independent analytical examination show that methotrexate prepared by the simple procedure given above is obtained in a better state of purity than present USP methotrexate.

EXAMPLE 3

N-[4-[[(2,4-Diamino-6-pteridinyl)methyl]amino]benzoyl]-L-glutamic Acid (3, Aminopterin) Hydrate (4:7)

A mixture of I (168 mg, 0.500 mmole) and N-(4-aminobenzoyl)-L-glutamic acid (400 mg. 1.50 mmoles) in DMAC (2 ml) was stirred at 25° under $N_2$ in a stoppered flask protected from light. Solution occurred after 2 hrs. After 18 hrs, the orange solution was mixed with $H_2O$ (15 ml) with stirring to give a finely divided, yellow precipitate. The mixture was centrifuged, and the supernatant removed by decantation. The yellow solid was stirred with four 15-ml portions of $H_2O$, each of which was removed by decantation after centrifugation. The solid was then suspended in EtOH (15–20 ml), collected by filtration, washed with $Et_2O$, and dried in vacuo (25°, $P_2O_5$) to give hydrated 3 in 68% yield (160 mg). Anal. Calcd for $C_{19}H_{20}N_8O_5 \cdot 1.75H_2O$: C, 48.36; H, 5.02; N, 23.74. Found: C, 48.72; H, 4.91; N, 23.36. Spectral data: λ max, nm ($\epsilon \times 10^{-3}$), 0.1 N HCl, 244 (18.2), 290 (20.5), 335 (11.0); pH 7, 260 (26.7), 283 (25.5), 370 (8.00); 0.1 N NaOH, 260 (26.9), 283 (25.3), 370 (8.00); pmr (DMSO-$d_6$), δ2.02 (m, 2, CHCH$_2$CH$_2$), 2.32 (m, 2, CH$_2$ CO$_2$H), 4.36 (m, 1, NHCHCO$_2$H), 4.52 (s, 2, CH$_2$N), 6.85 (m, 4, 2 phenylene protons plus NH$_2$), 7.72 (m, 2, phenylene), 7.86 (broad s, 2, NH$_2$), 8.13 (d, 1, NHCO), 8.72 (s, 1, C$_7$-H). Examination by tlc revealed one uv-absorbing spot and no fluorescence at any point. The uv data given above is in agreement with reported results.

EXAMPLE 4

N-[4-[[(2,4-Diamino-6-pteridinyl)methyl]amino]-phenylacetyl]-L-glutamic Acid (4) Monohydrate Treatment of N-(4-aminophenylacetyl-L-glutamic acid (5.60 g, 20.0 mmoles) with I (2.24 g, 6.67 mmoles) in DMAC (25 ml) as described for the preparation of 3 was followed by dropwise addition of the dark-orange reaction solution to stirred $H_2O$ (250 ml). Orange solid separated, and the mixture was stirred at 25° for 30 min and then at about 5° for 1 hr before the precipitate was collected by filtration. The suction-dried solid was removed from the funnel and stirred with $H_2O$ (125 ml). This mixture was centrifuged, and the clear supernatant was removed by decantation. After a second wash with $H_2O$ followed by centrifugation and decantation, the residue was again suspended in $H_2O$ and collected by filtration. The suction-dried solid was then washed with $Et_2O$ before it was dried in vacuo (25° over $P_2O_5$); yield 72% (2.27 g). Anal. Calcd for $C_{20}H_{22}N_8O_5 \cdot H_2O$: C, 50.84; H, 5.12; N, 23.72. Found: C, 51.00; H, 4.90; N, 24.02. Spectral data: λ max, nm ($\epsilon \times 10^{-3}$), 0.1 N HCl, 246 (18.3), 337 (10.1); pH 7, 256 (31.1), 370 (7.52); 0.1 N NaOH, 256 (31.8), 370 (7.57); pmr (DMSO-$d_6$), δ1.90 (m, 2, CHCH$_2$CH$_2$), 2.28 (m, 2, CH$_2$CO$_2$H), 3.32 (s, 2, CH$_2$CON), 4.22 (m, 1, NHCHCO$_2$H), 4.44 (s, 2, CH$_2$N), 6.66 (m, 4, 2 phenylene protons plus NH$_2$), 7.02 (m, 2, phenylene), 7.32 (s, 1, CH$_2$NH), 7.84 (braod s, 2, NH$_2$), 8.15 (d, 1, NHCO), 8.72 (s, 1, C$_7$—H). Tlc revealed one uv-absorbing spot with a very thin and faintly fluorescent cap.

EXAMPLE 5

N-[4-[[(2,4-Diamino-6-pteridinyl)methyl]amino]hydrocinnamoyl]-L-glutamic Acid (5) Dihydrate A mixture of I (2.24 g, 6.67 mmoles) and N-(4-aminohydrocinnamoyl)L-glutamic acid (20.0 mmoles) in DMAC (25 Ml) was stirred at 25° under $N_2$ in a stoppered flask protected from light. The mixture gradually thinned but separation of a precipitate commenced just before solution has occurred. After 24 hrs, the mixture was poured into $H_2O$ (250 ml) to give a red-orange precipitate, which was readily collected by filtration, washed on the funnel with several portions of $H_2O$ followed for $Et_2O$, and dried in vacuo (25° over $P_2O_5$); yield 72% (2.44 g). Tlc revealed a fluorescent spot above the dark, uv-absorbing spot and also at the origin. The crude product was then stirred with $H_2O$ (80 ml), and 0.1 N NaOH (100 ml) was added with stirring. The dark-red solution that formed was treated with Norit, filtered (Celite), chilled to about 5°, and treated with 0.1 N HCl (100 ml). The orange precipitate that formed was collected by filtration, washed on the funnel with $H_2O$ followed by $Et_2O$, and dried in vacuo (25° over $P_2O_5$); yield 38% (1.27 g). Anal. Calcd for $C_{21}H_{24}N_8O_5 \cdot 2H_2O$: C, 50.00; H, 5.59; N, 22.21. Found: C, 50.38; H, 5.00; N, 22.42. (A sample obtained from a trial run in the manner and percentage yield stated above gave the following elemental analysis results. Anal. Found: C, 50.37, 50.40; H, 5.29, 5.12; N, 22.63, 22.37). Spectral data: λ max, nm ($\epsilon \times 10^{-3}$), 0.1 N HCl, 246 (19.4), 336 (10.8); pH 7, 256 (30.9), 370 (7.80); 0.1 N NaOH, 256 (31.3), 370 (7.76); pmr (DMSO-$d_6$), δ 1.88 (m, 2, CHCH$_2$CH$_2$), 2.1–2.8 (overlapping multiplets, 6, C$_6$H$_4$CH$_2$CH$_2$CO and CH$_2$CO$_2$H), 4.22 (m, 1, NHCHCO$_2$H), 4.42 (s, 2, CH$_2$N), 6.65 (m, 4, 2 phenylene protons plus NH$_2$), 6.69 (m, 2, phenylene), 7.80 (broad s, 2, NH$_2$), 8.05 (d, 1, NHCO), 8.70 (s, 1, C$_7$—H). Tlc showed one uv-absorbing sopt with a thin, faintly fluorescent cap and a barely discernible fluorsecent spot at the origin.

EXAMPLE 6

N-[4-[[(2,4-Diamino-6-pteridinyl)methyl]amino]benzenesulfonyl]-L-glutamic Acid (6), Magnesium Salt, Heptahydrate A solution of I (2.63 g, 7.82 mmoles) and N-(4-aminobenzenesulfonyl-L-glutamic acid (2.60 g, 8.60 mmoles) in hexamethylphosphoric triamide (50 ml) was kept at about 25° for 6 days and then added to $H_2O$ (150 ml) with stirring. The mixture was refrigerated for about 4 hrs before it was centrifuged. The dark gel-like precipitate was washed with $H_2O$ (three times with 25–30 ml portions) until the clear supernatant following centrifugation became pale-yellow (as opposed to dark-orange initially). The precipitate, still as dark hydrous gel, was stirred with $H_2O$ (120 ml) and treated with NaOH solution (2 ml of 4 N). The dark-orange solution that formed was treated with Norit and filtered (Celite mat) to give a pale-orange filtrate which was treated with glacial ACOH to produce pH 4.0. A yellow gel-like precipitate formed. Following overnight refrigeration, the mixture was centrifuged and the residue was washed once with $H_2O$ as before and then Me$_2$CO. Following decantation after centrifugation from the Me$_2$CO wash, the residue was again suspended in Me$_2$CO, collected by filtration, washed with Me$_2$CO followed by $Et_2O$, and dried in vacuo (25°, $P_2O_5$) to give crude 6 as a brown solid (1.29 g). This material was treated in boiling $H_2O$ (100 ml) with MgO (500 ml) with rapid stirring, and, after about 5 min all the brown solid had dissolved. The hot mixture was clarified (Norit, Celite,) and the clear yellow filtrate was refrigerated overnight while the Mg salt of 6 separated as a yellow-solid. The mixture was centrifuged, and the Mg salt was washed once with cold $H_2O$ (20 ml). After centrifugation, the wash solution and the first decantate were combined and set aside for further processing. The solid was then suspended in Me$_2$CO, collected by filtration, washed with $Et_2O$, and air dried to constant weight (0.95 g) before it was recrystallized from the minimum volume of hot $H_2O$ (about 30 ml) to give the pure Mg salt as pale-yellow lustrous crystals, which were collected as before and dried in vacuo (25°, $P_2O_5$). The sample was then allowed to equilibrate with ambient conditions of the laboratory whereupon it underwent a weight increase (from 0.60 g to 0.76 g) that corresponds to transformation of the anhydrous salt to a heptahydrate. Elemental analysis results agree with that indication. The yield was 16%. Anal. Calcd for $C_{18}H_{18}MgN_8O_6S.7H_2O$: C, 34.60; H, 5.16; Mg, 3.89; N, 17.93. Found: C, 34.28; H, 5.24; Mg, 3.64; N, 17.67. Spectral data: $\lambda$ max, nm ($\epsilon \times 10^{-3}$), 0.1 N HCl, 245 (17.3), 272 (25.0), 337 (10.6); pH 7, 266 (33.5), 370 (7.82); 0.1 N NaOH, 263 (35.4), 372 (8.04); pmr ($CF_3CO_2D$), $\delta$ 2.25 (m, 2, $CHCH_2CH_2$), 2.73 (m, 2, $CH_2CO_2H$), 4.36 (m, 1, $NHCHCO_2H$), 5.30 (s, 2, $CH_2N$), 7.85 and 8.18 (m, 4, $C_6H_4$), 9.02 (s, 1, $C_7$—H). The sample was homogeneous according to tlc (one uv-absorbing spot).

The filtrate from the recrystallization step and the decantate from the centrifugation step were combined, and the pH of the solution was lowered by addition of AcOH from 8.5 to 4.0 to give the acid 6 as a pale-yellow solid (0.45 g). Examination of this product by tlc with the pure Mg salt as reference showed the acid to contain impurities that produced pale fluorescent streaks above and below the expected uv-absorbing spot. Further purification of the free acid was not pursued since the pure Mg salt was suitable for testing purposes.

EXAMPLE 7

N-[[5-[[(2,4-Diamino-6-pteridinyl)methyl]amino]-2-pyridinyl]-carbonyl]-L-glutamic acid (7, 2'-Azaaminopterin) Monohydrate Diethyl N-[(5-amino-2-pyridinyl)carbonyl]-L-glutamate (3.076 g, 9.5 mmoles) and I (3.19 g, 9.5 mmoles) were dissolved in dry DMAC (40 ml). The flask was flushed with $N_2$ and sealed, and the reaction mixture was stirred at about 25° for 7 days in the dark. The DMAC was removed by evaporation in vacuo, and the residue was dissolved in a solution consisting of $H_2O$ (230 ml), EtOH (200 ml), and NaOH solution (48 ml of 1 N). This solution was kept in a stoppered flask under $N_2$ at about 25° for 6 hrs. The solution was then neutralized to pH 7, and the EtOH was evaporated in vacuo. The volume of the aqueous solution remaining was increased to 500 ml, and the precipitate obtained by acidification to pH 4 was isolated and washed with $H_2O$ by centrifugation. The wet cake was freeze-dried to a brown solid (3.85 g). A solution (pH 8) of 3.2 g of this material in dilute KOH solution (200 ml) was treated with Norit and then filtered through Celite. The filtrate was neutralized to pH 7, and the Norit treatment was repeated. The resulting filtrate was acidified to pH 4, and the precipitate was isolated and washed with $H_2O$ by centrifugation. Treatment of the wet cake with $Me_2CO$ afforded a solid (1.64 g) which was isolated by filtration. This solid was purified by column chromatography using DEAE-cellulose (Mannex Regular Low Capacity; column dimensions 4.2 × 51 cm) prepared in the following manner. The dry DEAE-cellulose (150 gm) was hydrated, and the fines were removed so that about one-half of the original DEAE-cellulose remained. This material was deaerated, poured into the column and then washed successively with potassium phosphate buffer of pH 7.0 (3 l.), $H_2O$ (10 l.), and 0.2 M aqueous 2-mercaptoethanol (2 l.). The crude product was dissolved in dilute aqueous KOH (1.5 l.) which was 0.2 M in 2-mercaptoethanol, and this solution (pH 6.5) was applied to the column. The column was washed with 0.2 M aqueous 2-mercaptoethanol (1 l.) and then eluted using a stepwise gradient (0.1–0.3 M) of NaCl solutions of pH 7.0, 0.2 M in 2-mercaptoethanol and 0.005 M in potassium phosphate buffer. The uv absorbance of the column eluate was monitored continuously at 300 nm. The product moved down the column as a yellow-orange zone, and the product-containing fractions were divided into four groups according to their uv absorbance. Each fraction group was acidified (1 N HCl) to pH 4 and refrigerated. The individual precipitates were isolated by centrifugation and redissolved in $H_2O$ (200 ml) containing 2-mercaptoethanol (2 ml) by the addition of 1 N KOH to pH 8. These solutions were filtered, and the filtrates were acidified to pH 4 and refrigerated. The yellow precipitates were isolated and washed with $H_2O$ (four times) by centrifugation. The supernatant solutions were retained for lyophilization, and the wet precipitates were freeze-dried to yellow amorphous solids. On the basis of tlc analysis, three of these solids were combined (220 mg). The fourth solid and the solid obtained by lyophilization of the combined supernatant washes were redissolved in dilute KOH solution as before, and these solutions (pH 7) were treated with Norit and filtered. Acidification of the filtrates, and isolation and freeze-drying of the precipitates as before afforded an additional 178 mg of product. The total yield was 11% (398 mg). Anal. Calcd for $C_{18}H_{19}N_9O_5.H_2O$: C, 47.06; H, 4.61; N, 27.44. Found: C, 47.08; H, 4.58; N, 27.51. Spectral data: $\lambda$ max, nm ($\epsilon \times 10^{-3}$), 0.1 N HCl, 223 (22.3). 242 (21.6), 290 (19.2), 342 (18.9); pH 7, 259 (24.6), 282 (21.4), 305 (sh), 370 (7.94); 0.1 N NaOH, 259 (24.7), 282 (21.1), 305 (sh), 370 (8.13); pmr ($CF_3CO_2D$), $\delta$ 2.00–2.67 (overlapping multiplets, 4, $CH_2CH_2$), 5.00 (s, 2, $CH_2N$), 5.07 (m, 1, $NHCHCO_2H$), 7.90 (doublet of doublets, 1, $C_{5'}$—H), 8.43 (d, 1, $C_{6'}$—H), 8.47 (d, 1, $C_{3'}$—H), 9.05 (s, 1, $C_7$—H).

EXAMPLE 8

N-[[4-[[(2,4-Diamino-6-pteridinyl)methyl]amino]-phenyl]acetyl]-L-aspartic Acid (8) Hemihydrate N-[(4-Aminophenyl)acetyl]-L-aspartic acid (2.34 g, 8.8 mmoles) and I (2.69 g, 8 mmoles) were dissolved in DMAC (40 ml). The flask was flushed with $N_2$ and closed, and the reaction mixture was stirred at about 25° for 4 days in the dark. The reaction mixture was filtered, and the solid on the funnel was washed with DMAC. The filtrate was treated with $H_2O$ (250 ml), and the suspended product was dissolved by addition of the minimum of 1 N NaOH. The solution (pH 7.5) was treated with Norit and filtered through Celite. The filtrate was acidified to pH 6.2, and the mixture was clarified (Norit, Celite) as before. Acidification of the filtrate to pH 4 afforded an orange precipitate, which was isolated by centrifugation and then redissolved as before by addition of 1 N NaOH as required to a suspension in $H_2O$ (250 ml). This solution was acidified to pH 6.3 and clarified (Norit, Celite) once more. The filtrate was acidified to pH 3.9 and refrigerated. The orange precipitate was isolated and washed with cold $H_2O$ (four times) by centrifugation. The wet product was lyophilized, pulverized, and dried further in vacuo over $P_2O_5$ for 24 hrs; yield 37% (1.3 g). Anal. Calcd for $C_{19}H_{20}N_8O_5.0.5H_2O$: C, 50.78; H, 4.71; N, 24.93. Found: C, 50.69; H, 4.72; N, 25.09. Spectral data: $\lambda$ max, nm ($\epsilon \times 10^{-3}$), 0.1 N HCl, 246 (19.6), 291 (5.69), 337 (10.3), 349 (sh); pH 7, 257 (31.7), 370 (7.49); 0.1 N NaOH, 257 (32.4), 370 (7.92); pmr ($CF_3CO_2D$), $\delta$ 3.27 (m, 2, $CH_2CO_2H$), 3.93 (s, 2, $C_6H_4CH_2CO$), 5.17 (m, 1, CHNH), 5.23 (s, 2, CH$_2$NH); 7.60 (s, 4, C$_6$H$_4$), 9.0 (s, 1, C$_7$—H).

EXAMPLE 9

4-[N-[4-[[(2,4-diamino-6-pteridinyl)methyl]amino]benzoyl]amino]-butyric Acid (9) Hydrobromide Hydrate with N,N-Dimethylacetamide (20:20:12:5)

A suspension of 4-(4-nitrobenzamido)butyric acid (1.12 g, 4.75 mmoles) in H$_2$O (55 ml) was hydrogenated in the presence of a 5% palladium-on-charcoal catalyst at room temperature and atmospheric pressure. The catalyst was removed by filtration, and the filtrate was evaporated to dryness in vacuo. The resulting residue of 4-(4-aminobenzamido)butyric acid (1.02 g) was dissolved in DMAC (10 ml) containing I (504 mg, 1.50 mmoles), and the whole was stirred at about 25° for 60 hrs. The precipitate of the product was collected by filtration, washed with Et$_2$O and dried in vacuo (78°, P$_2$O$_5$) for 68 hrs; yield 63% (483 mg). This sample decomposed from about 240° (Mel-Temp) and was homogeneous by tlc (5:1 CHCl$_3$—MeOH). Anal. Calcd for C$_{18}$H$_{20}$N$_8$O$_3$.HBr.0.60H$_2$O.0.25 DMAC: C, 44.75; H, 4.83; N, 22.66. Found: C, 44.54; H, 4.81; N, 22.34. Spectral data: λ max, nm ($\epsilon \times 10^{-3}$), 0.1 N HCl, 244 (16.6Z); 287 (16.9), 337 (9.58); pH 7, 261 (24.4), 279 (22.4), 370 (6.82); 0.1 N NaOH, 260 (24.7 ), 279 (22.6), 370 (7.06); pmr (DMSO-d$_6$), δ 1.72 (m, 2, CH$_2$CH$_2$CH$_2$), 2.25 (m, 2, CH$_2$CO$_2$H), 3.23 (m, 2, CONHCH$_2$), 4.63 (s, 2, CH$_2$N), 7.22 (m, 4, C$_6$H$_4$), 8.09 (m, 1, NHCO), 8.86 (s, 1, C$_7$—H), 9.34 (NH). The pmr spectrum also showed the presence of DMAC; the NH$_2$ and CO$_2$H groups were too broad to locate but are observed in the integral.

EXAMPLE 10

N-[4-[[(2,4-Diamino-6-pteridinyl)methyl]amino]benzoyl]glycine (10) Sesquihydrate A solution of I (1.01 g, 3.00 mmoles) and N-(4-aminobenzoyl)glycine (640mg, 3.30 mmoles) in DMAC (10 ml) was stirred under N$_2$ in a stoppered flask protected from light for 4 days. The yellow precipitate that formed was collected by filtration, washed with DMAC (twice with 4-ml portions), suspended in H$_2$O (200 ml), and dissolved by addition of the required volume of 1 N KOH. The solution (pH 11) was treated with Norit and filtered (Celite mat). The filtrate was brought to 400 ml volume, acidified to pH 4 by addition of 1 N HBr, and refrigerated. The yellow precipitate that formed was isolated and washed (four times) with H$_2$O by centrifugation. The solid was finally suspended in Me$_2$CO (350 ml), collected by filtration, and dried in vacuo; yield 55% (604 mg). Anal. Calcd for C$_{16}$H$_{16}$N$_8$O$_3$.1.5H$_2$O: C, 48.60; H, 4.84; N, 28.34. Found: C, 48.82; H, 4.85; N, 28.40. Spectral data: $\lambda_{max}$, nm ($\epsilon \times 10^{-3}$), 0.1 N HCl, 244 (18.0), 288 (20.7), 336 (11.2), 348 (sh); pH 7, 260 (27.5), 282 (25.4), 371 (8.20); 0.1 N NaOH, 260 (27.1), 282 (25.4), 371 (8.20); pmr (CF$_3$CO$_2$D), δ 4.50 (s, 2, CH$_2$CO$_2$H), 5.34 (s, 2, CH$_2$N), 8.00 (m, 4, C$_6$H$_4$), 9.04 (s, 1, C$_7$—H).

EXAMPLE 11

4-[[(2,4-Diamino-6-pteridinyl)methyl]methylamino]-benzoic Acid (11) Sesquihydrate A solution of I (168 mg, 0.500 mmole ) and 4-(methylamino)benzoic acid (83 mg, 0.55 mmole) in DMAC (2ml) was stirred at about 25° for 114 hrs and then mixed with H$_2$O (18 ml) to cause separation of 11. The collected and dried solid (150 mg) was reprecipitated from Norit-treated and filtered (Celite) NaOH solution (7.5 ml of 0.08 N) by treatment with 1 N HCl to produce pH 6.5. The yellow solid was collected, washed with H$_2$O, and dried in vacuo (78° over P$_2$O$_5$); yield 60% (105 mg). Anal. Calcd for C$_{15}$H$_{15}$N$_7$O$_2$.1.5H$_2$O: C, 51.13; H, 5.15; N, 27.83. Found: C, 51.02; H, 5.24; N, 27.52. Spectral data: $\lambda_{max}$, nm ($\epsilon \times 10^{-3}$), 0.1 N HCl, 240 (17.7), 311 (25.9), 350 (sh) (9.83); pH 7, 258 (25.4), 285 (22.9), 372 (7.21); 0.1 N NaOH, 258 (25.8), 285 (22.9), 372 (7.48); pmr (DMSO-d$_6$), δ 3.23 (s, 3, CH$_3$N), 4.82 (s, 2, CH$_2$), 6.74 (s, 2, NH$_2$), 6.84 and 7.76 (m, 4, C$_6$H$_4$), 7.58 (very broad s, 2, NH$_2$), 8.60 (s, 1, C$_7$—H). The uv and pmr spectral data listed are in good agreement with reported data for a sample that gave satisfactory elemental analysis results for 11.0.65 HCl, and, surprisingly, the ir spectrum of that sample is identical with that of 11.1.5 H$_2$O described above. Examination of 11.1.5H$_2$O by tlc revealed one uv-absorbing spot with a barely discernible fluorescent spot just above it.

EXAMPLE 12

4-[[2,4-Diamino-6-pteridinyl]methyl]aminobenzamide (12) Hydrobromide Monohydrate A solution of I (500 mg, 1.49 mmoles) and 4-aminobenzamide (410 mg, 2.98 mmoles) in DMAC (20 ml) was stirred at about 25° for 20 hrs. The deposit of bright yellow solid was collected by filtration, washed with cold DMAC, and dried in vacuo (25°, P$_2$O$_5$); yield 330 mg. Evaporation of the filtrate gave a solid residue that was washed thoroughly with Et$_2$O and EtOH; yield 220 mg. The two crops produced identical thin-layer chromatograms and were combined; total yield 94% (550 mg). Treatment of a finely ground suspension of this solid with 0.5 M NaHCO$_3$ solution resulted in incomplete removal of HBr. The recovered solid (0.40 g) was converted to the full hydrobromide salt by suspending it in EtOH (20 ml), adding 48% HBr (0.10 ml), and diluting slowly with Et$_2$O (200 ml). The yellow solid was dried in vacuo (78°, P$_2$O$_5$); yield 62% (380 mg); mp chars, but does not melt below 350° (Mel-Temp). Anal. Calcd for C$_{14}$H$_{14}$N$_8$O.HBr.H$_2$O; C, 41.09; H, 4.19; N, 27.38; Br, 19.52. Found: C, 41.23; H, 3.69; N, 27.44; Br, 19.73. Spectral data: $\lambda_{max}$, nm ($\epsilon \times 10^{-3}$), 0.1 N HCl, 243 (17.5), 289 (19.2), 336 (11.2); pH 7, 259 (25.0), 284 (21.6), 371 (7.9); 0.1 N NaOH, 259 (25.6). 284 (21.6). 371 (8.2); pmr (DMSO-d$_6$), δ 4.59 (s, 2, CH$_2$N), 7.22 (m, C$_6$H$_4$ and NH$_2$), 8.81 (m, 3, NH$_2$ and C$_7$—H).

EXAMPLE 13

4-[[(2,4-Diamino-6-pteridinyl)methyl]amino]-N-propylbenzamide (13) Hydrobromide A solution of 4-nitro-N-propylbenzamide (1.00 g, 4.80 mmoles) in MeOH (25 ml) was hydrogenated in the presence of a 5% palladium-on-charcoal catalyst at about 25° and atmospheric pressure. The catalyst was removed by filtration, and the filtrate was evaporated to dryness in vacuo to give 4-amino-N-propylbenzamide as a gummy residue; yiel 836 mg. This product was dissolved in DMAC (10 ml) containing I (504 mg, 1.50 mmoles), and the whole was stirred at room temperature for 72 hrs. The precipitate of the product was collected by filtration, washed with Et$_2$O and dried in vacuo over P$_2$O$_5$; yield 74% (482 mg), mp > 340° (Mel-Temp). This sample was homogeneous on tlc (5:1 CHCl$_3$-MeOH). Anal. Calcd for C$_{17}$H$_{20}$N$_8$O.HBr: C, 47.12; H, 4.88; N, 25.86. Found: C, 47.10; H, 5.18; N, 25.55. Spectral data: $\lambda_{max}$, nm ($\epsilon \times 10^{-3}$), 0.1 N HCl, 244 (18.5), 284 (18.3), 337 (10.5), 345 (sh) (9.70); pH 7, 261 (26.9), 279 (24.2), 371 (7.65); 0.1 N NaOH, 261 (27.1), 279 (24.2), 371 (7.73); δ 0.96 (t, 3, CH$_3$), 1.50 (m, 2, CH$_2$CH$_3$), 3.17 (m, 2, NHCH$_2$CH$_2$), 4.62 (s, 2, CH$_2$N), 7.23 (m, 4, C$_6$H$_4$), 8.07 (m, 1, NHCO), 8.87 (s, 1, C$_7$—H), 9.35 (NH). Some of the NH$_2$ peaks were too broad to locate but are observed in the integral.

EXAMPLE 14

4-[[2,4-Diamino-6-pteridinyl]methyl]amino-N,N-dimethylbenzamide (14) Hydrobromide Hydrate

A solution of I (500 mg, 1.49 mmoles) and 4-amino-N,N-dimethylbenzamide (740 mg, 4.47 mmoles) in DMAC (20 ml) was stirred at about 25° for 48 hrs. The solution, which had become turbid after about 24 hrs, was evaporated to dryness in vacuo. The yellow residue was triturated thoroughly with several portions of Et$_2$O. The finely pulverized solid was stirred with H$_2$O (40ml), and the mixture was adjusted to pH 7.5 with 1 N NaOH. The insoluble solid was collected by filtration and washed with H$_2$O by centrifugation. Elemental analysis results showed that the material obtained had been only partially converted to the free base. The product obtained in 56% yield (330 mg) underwent gradual decomposition without melting above 220° (Mel-Temp). Anal. Calcd for C$_{16}$H$_{18}$N$_8$O.0.52HBr.H$_2$O: C, 48.23; H, 5.19; Br, 10.43; N, 28.12. Found: C, 48.40; H, 5.07; Br, 10.47; N, 28.28. Spectral data: $\lambda_{max}$, nm ($\epsilon \times 10^{-3}$), 0.1 N HCl, 245 (21.3), 275 (12.8), 336 (10.7); pH 7, 261 (30.9), 372 (7.7); 0.1 N NaOH, 260 (32.1), 372 (7.9); pmr (DMSO-d$_6$), δ 2.94 (s, 6, CH$_3$), 4.42 (broad overlapping multiplets, CH$_2$, NH, H$_2$O), 7.01 (m, C$_6$H$_4$, NH$_2$), 8.51 (s, 2, NH$_2$), 8.78 (s, 1, C$_7$—H).

EXAMPLE 15

6-[(4-Acetylphenylamino)methyl]-2,4-pteridinediamine (15) Hydrobromide

A magnetically stirred mixture of I (1.01 g, 3.00 mmoles) and 4-aminoacetophenone (1.62 g, 12.0 mmoles) in DMAC (20 ml) in a centrifuge tube became clear within 15 min, and 15.HBr began separating after 30 min. The mixture was stirred 20 hrs at 25° (stoppered under N$_2$ and protected from light) before it was centrifuged. Successive washes of the orange solid with DMAC (5 ml) and EtOH (three times with 15-ml portions) were each followed by centrifugation and decantation. The residue was finally stirred with Et$_2$O, collected by filtration, and dried in vacuo (25°, P$_2$O$_5$); yield 68% (0.80 g). Anal. Calcd for C$_{15}$H$_{15}$N$_7$O.HBr: C, 46.17; H, 4.13; N, 25.12. Found: C, 46.45; H, 4.29; N, 25.38. Spectral data: $\lambda_{max}$, nm ($\epsilon \times 10^{-3}$), 0.1 N HCl, 241 (20.3), 327 (27.8); pH 7, 258 (22.0), 327 (24.1); 0.1 N NaOH, 258 (22.1), 327 (24.1); pmr (CF$_3$CO$_2$D), δ 2.84 (s, 3, CH$_3$), 5.36 (s, 2, CH$_2$N, 7.98 and 8.33 (m, 4, C$_6$H$_4$), 9.08 (s, 1, C$_7$—H).

EXAMPLE 16

N-[4-[(2,4-Diamino-6-pteridinyl)methylamino]phenyl]-acetamide (16) Hydrate

A mixture of I (336 mg, 1.00 mmole) and 4′-aminoacetanilide (451 mg, 3.00 mmoles) in hexamethylphosphoric triamide (6 ml) was stirred for 22 hrs and poured into H$_2$O (25 ml) containing 1 N NaOH (2.0 ml). The resulting mixture was stirred in an ice bath and the orange precipitate collected, washed successively with H$_2$O, 4:1 Et$_2$O-MeOH and Et$_2$O and dried in vacuo (100°, P$_2$O$_5$); yield 69% (240 mg), mp > 260° (Kofler Heizbank). Anal. Calcd for C$_{15}$H$_{16}$N$_8$O.1.2H$_2$O: C, 52.08; H, 5.36; N, 32.39. Found: C, 51.99; H, 4.94; N, 32.38. Spectral data: $\lambda_{max}$, nm ($\epsilon \times 10^{-3}$), 0.1 N HCl, 246 (30.8), 336 (10.9), 350 (sh) (9.52); pH 7, 259 (33.0), 372 (7.62); 0.1 N NaOH, 259 (34.1), 373 (7.81); pmr (DMSO-d$_6$), δ 1.96 (s, 3, COCH$_3$), 4.42 (d, 2, CH$_2$N), 6.12 (s, 1, NHCH$_2$), 6.57, 7.72 (d, NH$_2$), 6.66 and 7.32 (m, 4, C$_6$H$_4$), 8.71 (s, 1, C$_7$—H), 9.52 (s, 1, NHCO).

EXAMPLE 17

N-[2-[4-[[(2,4-diamino-6-pteridinyl)methyl]amino]-phenyl]ethyl]acetamide (17) Hydrobromide Dihydrate

A solution of N-[2-(4-aminophenyl)ethyl]acetamide (713 mg, 4 mmoles) and I (672 mg, 2 mmoles) in DMAC (8 ml) was stirred under N$_2$ at about 25° in a stoppered flask protected from light for 2 days. The precipitate was isolated by filtration and the solid on the funnel was washed with DMAC (2 × 4 ml). The filtrate was set aside, and the solid was then washed with EtOH (5 ml) and H$_2$O (2 × 3 ml). The addition of an equal volume of H$_2$O to the DMAC filtrate afforded more product which was isolated by filtration and washed with H$_2$O. Evaporation of the EtOH-H$_2$O washes also afforded more product, which was triturated with Et$_2$O and isolated by filtration. The combined yield was 70% (609 mg). A sample obtained in this manner was recrystallized from MeOH to give the pure product in about 50% recovery. Anal. Calcd for C$_{17}$H$_{20}$N$_8$O.HBr.2H$_2$O: C, 43.50; H, 5.37; N, 23.88. Found: C, 43.40; H, 5.42; N, 23.82. Spectral data: $\lambda_{max}$, nm ($\epsilon \times 10^{-3}$), 0.1 N HCl, 246 (17.9), 292 (5.80), 337 (10.2), 347 (sh); pH 7, 257 (27.6), 280 (sh), 372 (7.70); 0.1 N NaOH, 257 (28.6), 280 (sh), 372 (7.96); pmr (DMSO-d$_6$), δ 1.76 (s, 3, CH$_3$), 2.56 (m, 2, C$_6$H$_4$—CH$_2$CH$_2$), 3.16 (m, 2, CH$_2$NHCO), 4.52 (s, 2, CH$_2$NHC$_6$H$_4$), 6.80 (m, 4, C$_6$H$_4$), 8.84 (s, 1, C$_7$—H).

EXAMPLE 18

6-[[(4-Methoxyphenyl)amino]methyl]-2,4-pteridinediamine (18) Hydrobromide

A solution of I (2.69 g, 8.00 mmoles) and freshly recrystallized 4-methoxybenzeneamine (1.97 g, 16.0 mmoles) in DMAC (26 ml) was stirred under N$_2$ at about 25° in a stoppered flask protected from light for 3 days. The product that separated was collected under N$_2$ in subdued light, and washed with DMAC, H$_2$O, and EtOH. Subsequent operations were also carried out in subdued light and under N$_2$ whenever possible. The solid was dried in vacuo (25°, P$_2$O$_5$) to give crude 18.HBr in 56% yield (1.68 g). Recrystallization of part (1.28 g) of this material from MeOH led to two crops of brick-red 18.HBr (555 and 219 mg). The second smaller crop was slightly less pure than the first, which gave the following analytical results. Anal. Calcd for C$_{14}$H$_{15}$N$_7$O.HBr.0.1CH$_3$OH: C, 44.40; H, 4.33; N, 25.70. Found: C, 44.59; H, 4.12; N, 25.94. Spectral data: $\lambda_{max}$, nm ($\epsilon \times 10^{-3}$), 0.1 N HCl, 246 (19.0), 337 (10.6), 348 (sh); pH 7, 257 (26.6), 280 (sh), 3.72 (7.70); 0.1 N NaOH, 257 (27.1), 280 (sh), 372 (7.80); pmr (DMSO-d$_6$), δ 3.17 (s, CH$_3$OH solvate), 3.64 (s, 3, CH$_3$O), 4.50 (s, 2, CH$_2$N), 6.73 (m, 4, C$_6$H$_4$), 8.86 (s, 1, C$_7$—H).

EXAMPLE 19

6-[(4-Chloroanilino)methyl]-2,4-pteridinediamine (19)

Compound I (336 mg, 1.00 mmole) was added to a solution of 4-chloroaniline (383 mg, 3.00 mmoles) in DMAC (5 ml), and the resulting mixture was stirred under N₂ for 17 hrs and poured into H₂O (25 ml). The yellow precipitate of crude hydrobromide was collected by filtration, washed with H₂O, then Et₂O and dried in vacuo (P₂O₅). A suspension of the hydrobromide (339 mg) in H₂O (30 ml) containing 1 N NaOH (1.80 ml) was stirred for 3 hrs. The yellow product was collected, washed with H₂O, then Et₂O, and dried at 100° in vacuo (P₂O₅); yield 85% (255 mg), mp > 360° (Kofler Heizbank). Anal. Calcd for $C_{13}H_{12}ClN_7$: C, 51.75; H, 4.01; N, 32.49. Found: C, 51.65; H, 4.15; N, 32.78. Spectral data: $\lambda_{max}$, nm ($\epsilon \times 10^{-3}$), 0.1 N HCl, 246 (21.3), 290 (sh) (5.81), 237 (10.5), 350 (sh) (9.16); pH 7, 257 (33.1), 371 (7.86); 0.1N NaOH (unstable); pmr (DMSO-$d_6$), δ 4.44 (d, 2, CH₂), 6.46 (m, NH), 6.60, 7.73 (d, NH₂), 6.73 and 7.14 (m, 4, C₆H₄), 8.72 (s, 1, C₇—H).

EXAMPLE 20

6-[(N-Methylanilino)methyl]-2,4-pteridinediamine (20)

A solution of I (500 mg, 1.49 mmoles) and excess freshly distilled N-methylaniline (5 ml) in DMAC (20 ml) was stirred at about 25° for 48 hrs. The yellow solid that precipitated was collected by filtration, washed with cold DMAC and dried in vacuo (25°, P₂O₅); yield 26% (110 mg). The solid was stirred for a few minutes with cold 0.5 M NaHCO₃ solution (25 ml), collected by filtration, and washed by centrifugation. Recrystallization from hot EtOH (50 ml) gave a fluorescent yellow powder; yield 7% (30 mg), mp 277°–268° dec. (Mel-Temp). Anal. Calcd for $C_{14}H_{15}N_7$: C, 59.77; H, 5.38; N, 34.85. Found: C, 59.99; H, 5.47; N, 34.64. Spectral data: $\lambda_{max}$, nm ($\epsilon \times 10^{-3}$), 0.1 N HCl, 247 (15.5), 290 (sh), 337 (13.6), 350 (sh); pH 7, 257 (26.7), 371 (6.32); 0.1 N NaOH, 257 (27.2), 371 (6.61); pmr (DMSO-$d_6$), δ 3.10 (s, 3, CH₃), 4.68 (s, 2, CH₂N), 6.88 (m, 7, NH₂ and C₆H₅), 7.54 (s, 2, NH₂), 8.53 (s, 1, C₇—H).

The filtrate from the 110 mg crop was evaporated to give a yellow residue which was washed thoroughly with Et₂O and EtOH and then dried; yield 0.34 g. Treatment with NaHCO₃ solution and recrystallization from EtOH as described above gave additional 20, mp 258°–260° dec (Mel-Temp), in 57% yield (240 mg). Anal. Calcd for $C_{14}H_{15}N_7$: C, 59.77; H, 5.38; N, 34.85. Found: C, 59.66; H, 5.30; N, 34.67.

EXAMPLE 21

6-[(Phenylamino)methyl]-2,4-pteridinediamine (21) Hydrobromide

Solid I (1.01 g, 3.00 mmoles) was added in 4 equal portions during 35 min (at intervals of sufficient time to allow the preceding portion to dissolve) to a stirred solution of freshly distilled aniline (1.11 g, 12.0 mmoles) and DMAC (20 ml) at 20°–25°. A clear solution formed soon after the last addition, and then, after about 5 min, crystalline product began separating. The mixture was stirred 22 hrs longer with the reaction flask purged with N₂, stoppered, and protected from light. The collected yellow precipitate of 21.HBr was washed successively with cold H₂O, Me₂CO, and Et₂O; yield 79% (0.82 g). Recrystallization from H₂O (~ 250 ml required) afforded pure 21.HBr in 38% yield (0.40 g). Anal. Calcd for $C_{13}H_{13}N_7$.HBr: C, 44.84; H, 4.05; N, 28.16. Found: C, 45.09; H, 4.16; N, 27.96. Spectral data: $\lambda_{max}$, nm($\epsilon \times 10^{-3}$), 0.1 N HCl, 246 (18.4), 292-303 (plateau) (5.35), 336 (10.0), 350 (sh) (8.80); pH 7, 257 (27.2), 372 (7.24); 0.1 N NaOH, 257 (27.4), 372 (7.55); pmr (CF₃CO₂D), δ 5.28 (s, 2, CH₂), 7.6 (m, 5, C₆H₅), 9.02 (s, 1, C₇—H).

EXAMPLE 22

Dimethyl-N-[5-[[(2,4-diamino-6-pteridinyl)methyl]methylamino]-pentanoyl]-L-glutamate (22) Hemihydrate KOC₄H₉-t (6.55g, 58.4 mmoles) was added to a chilled solution containing I (4.91 g, 14.6 mmoles) and diethyl N-[5-(methylamino)pentanoyl]-L-glutamate hydrobromide (11.6 g, 29.2 mmoles) in DMAC (150 ml). The mixture was stirred at about 25° under N₂ in a closed flask protected from light for 19 hrs. The reaction mixture was filtered to remove insoluble matter, and the filtrate was evaporated in vacuo. The gummy residue was dissolved in MeOH (20 ml), and the solution was filtered and diluted with CHCl₃ (80 ml). This solution was applied to a silica gel column (450 g of Brickmann's Silica Gel H, Type 60), and the column was eluted with CHCl₃:MeOH (4:1). According to tlc results all fractions that contained product contained also some unreacted starting ester. These fractions were combined and evaporated. The semisolid residue was stirred with EtOH (20 ml), and the yellow solid that formed was collected. Addition of Et₂O (200 ml) to the filtrate gave more yellow solid, which was collected and washed with a little EtOH. The pmr and mass spectra of these two crops showed each to be the hydrobromide of the expected product; pmr (DMSO-$d_6$), δ 2.70 (s, 3, CH₃N), 4.05 (pair of quartets, 4, OCH₂), 1.17 (t, 6, OCH₂CH₃); m/e 490 (M⁺). An unsuccessful attempt was made to dissolve this material in warm MeOH for column chromatography as before. The MeOH was evaporated in vacuo, and the yellow residue was suspended in EtOH (50ml). KOC₄H₉-t was added in portions until solution occurred. The KBr formed was removed by filtration, and the filtrate was evaporated. The residue was dissolved in CHCl₃—MeOH (4:1, 50 ml), and the solution was applied to a silica gel column (120 g of Brickmann's Silica Gel H, Type 60). The column was eluted with 4:1 CHCl₃—MeOH, the tlc-homogeneous fractions were combined and evaporated in vacuo. The yellow solid that remained was triturated with Et₂O and dried in vacuo (25°, P₂O₅); yield 12% (816 mg) of product which had undergone transesterification to the corresponding dimethyl ester. Anal. Calcd for $C_{20}H_{30}N_8O_5.0.5H_2O$: C, 50.95; H, 6.63; N, 23.76. Found: C, 50.97; H, 6.43; N, 23.91. Spectral data: pmr (DMSO-$d_6$), δ 1.26–2.44 [overlapping multiplets, 12, (CH₂)₄CO and (CH₂)₂CO], 2.16 (s, 3, CH₃N), 3.56 (s, 3, CH₃O), 3.60 (s, 3, CH₃O), 3.64 (s, 2, CH₂NCH₃), 4.27 (m, 1, NHCHCO). 8.18 (d, 1, CONH), 8.73 (s, 1, C₇—H); mass spectrum, m/e 462 (M⁺).

EXAMPLE 23

N-[5-[[(2,4-diamino-6-pteridinyl)methyl]methylamino]-pentanoyl]-L-glutamic Acid (23) Dihydrochloride Sesquihydrate A solution of 22 (542 mg, 1.15 mmoles) in deaerated 0.1 N NaOH (92 ml) was stirred in the dark at about 25° in a closed flask under N₂ for 4 hrs. The solution was treated with 1 N HCl to produce pH 6 and diluted to 1 l. This solution was applied to a DEAE-cellulose column (4 × 25 cm; prepared from Mannex Regular Low Capacity DEAE-Cellulose by de-fining and deaerating) which had been treated with 0.5 M NaCl (1 l.), 0.5 NHCl (1 l.), 0.5 N NH₄OH (1 l.), and H₂O (6 l.). The uv absorbance of the column eluate was continuously monitored at 250 nm during application, washing, and elution. After application was complete, the column was washed with H$_2$O (1.2 l.). The product was eluted with 0.02 N HCl, and its travel on the column could be observed by means of its blue fluorescence in uv light. The product-containing fractions, which were strongly uv absorbing, were pooled and lyophilized. The solid thus obtained was dissolved in 50 ml of water, and this solution was filtered and lyophilized. The product was faintly yellow, very light and fluffy; yield 89% (549 mg). Anal. Calcd for C$_{18}$H$_{26}$N$_8$O$_5$.2HCl .1.5H$_2$O: C, 40.46; H, 5.85; N, 20.97; Cl, 13.27. Found: C, 40.49; H, 5.56; N, 20.80; Cl, 13.54. Spectral data: $\lambda_{max}$, nm ($\epsilon \times 10^{-3}$), 0.1 N HCl 246 (16.6), 297 (6.50), 337 (10.0), 348 (sh); pH 7, 225 (10.7), 262 (24.1), 373 (7.30); 0.1 N NaOH, 225 (12.1), 258 (24.3), 369 (7.50); pmr (DMSO-d$_6$), δ 1.4–2.4 [overlapping multiplets, 10, (CH$_2$)$_3$CO and (CH$_2$)$_2$CO], 2.78 (s, 3, CH$_3$N), 3.18 (m, 2, NCH$_2$CH$_2$), 4.20 (m, 1, NHCHCO), 4.69 (s, 2, PterCH$_2$NCH$_3$), 8.22 (d, 1, CONH), 8.96 (s, 1, C$_7$—H).

EXAMPLE 24

6-[(Phenethylamino)methyl]-2,4-Pteridinediamine (24)

Compound I (336 mg, 1.00 mmole) was added to a stirred solution of phenethylamine (970 mg, 8.00 mmoles) in DMAC (5 ml) at 0°, and the resulting suspension was stirred at 25° for 18 hrs and poured into H$_2$O (25 ml). The crude product was collected by filtration, washed with H$_2$O, dried in vacuo (100°, P$_2$O$_5$) and redissolved in DMAC (8 ml). The solution was diluted with H$_2$O (1 ml), stirred for 10 min, filtered and evaporated to dryness in vacuo. The residue of yellow solid was triturated with Et$_2$O and dried in vacuo (100°, P$_2$O$_5$); yield 59% (173 mg), mp about 219° dec (Kofler Heizback). Anal. Calcd for C$_{15}$H$_{17}$N$_7$: C, 61.00; H, 5.80; N, 33.20. Found: C, 60.98; H, 5.84; N, 33.10. Spectral data: $\lambda_{max}$, nm ($\epsilon \times 10^{-3}$), 0.1 N HCl, 246 (16.4), 293 (sh) (5.23), 337 (9.70), 350 (sh) (8.5); pH 7, 225 (11.5), 261 (23.4), 373 (7.13); 0.1 N NaOH, 258 823.4), 371 (7.09); pmr (DMSO-d$_6$), δ 2.78 (s, 4, CH$_2$CH$_2$), 3.90 (s, 2, PterCH$_2$N), 6.57, 7.29 (d, 4, NH$_2$), 7.23 (s, 5, C$_6$H$_5$), 8.72 (s, 1, C$_7$—H).

EXAMPLE 25

6-[[3-(2-Ethoxyethoxy)propylamino]methyl]-2,4-pteridinediamine (25)

A mixture of I (336 mg, 1.00 mmole) and 3-(2-ethoxyethoxy)propylamine (588 mg, 4.00 mmoles) in DMAC (5 ml) was stirred for 18 hrs, filtered, and evaporated to dryness in vacuo. A solution of the residue in MeOH (10 ml) was filtered and applied to two Brinkmann Silica Gel F-254 preparative thin-layer chromatography plates and developed with MeOH. The band of yellow product was extracted with hot MeOH and the extract evaporated to a solid which was triturated with Et$_2$O (2 ml) and dried in vacuo (100°, P$_2$O$_5$); yield 29% (95 mg), mp about 207° dec (Kofler Heizback). Anal. Calcd for C$_{14}$H$_{23}$N$_7$O$_2$.0.2H$_2$O: C, 51.74; H, 7.26; N, 30.17. Found: C, 51.70; H, 7.34; N, 30.25. Spectral data: $\lambda_{max}$, nm ($\epsilon \times 10^{-3}$), 0.1 N HCl, 245 (16.1), 290 (sh) (5.18), 336 (9.75), 350 (sh) (8.46); pH 7, 225 (11.5), 261 (23.0), 373 (7.17); 0.1 N NaOH, 225(12.2), 257 (23.3), 370 (7.34); pmr (DMSO-d$_6$), δ 1.07 (m, 3, CH$_3$), 1.67 (m, 2, CH$_2$CH$_2$CH$_2$), 2.59 (m, NCH$_2$CH$_2$), 3.40–3.64 (m, CH$_2$O), 3.85 (s, 2, PterCH$_2$N), 6.55, 7.60 (d, 4, NH$_2$), 8.74 (s, 1, C$_7$—H).

EXAMPLE 26

6-[(Cyclohexylamino)methyl]-2,4-pteridinediamine (26) Hemihydrate

Solid I (2.77 g, 8.30 mmoles) was added in 4 equal portions during 1 hr to a stirred solution of cyclohexaneamine (2.45 g, 24.8 mmoles) in DMAC (33 ml). The mixture was stirred 21 hrs at 25° with the reaction flask purged with N$_2$, stoppered, and protected from light. H$_2$O (400 ml) was added to the stirred reaction mixture, and the solution (pH 9.7) quickly deposited a yellow solid which was removed by filtration after 10 min. A small additional amount of solid was removed after 15 min longer. These two solids were discarded. The solution was now flushed thoroughly with N$_2$, and the pH of the solution was adjusted to 12 by the addition of 2 N NaOH. Gradual separation of yellow solid occurred during refrigeration for 45 min. The solid was collected, and the filtrate deposited more yellow precipitate over a period of one hour while N$_2$ was passed through the solution. The second crop of yellow solid was also collected. Both crops were washed with water and Et$_2$O before being dried in vacuo (25°, P$_2$O$_5$); total yield 46% (1.03 g). Anal. Calcd for C$_{13}$H$_{19}$N$_7$.0.5H$_2$O: C, 55.30; H, 7.14; N, 34.73. Found: C, 55.18; H, 7.14; N, 34.88. Spectral data: $\lambda_{max}$, nm ($\epsilon \times 10^{-3}$), 0.1 N HCl, 245 (17.9), 283 (9.15), 336 (10.4), 347 (sh); pH 7, 261 (24.0), 372 (7.10); 0.1 N NaOH, 257 (23.9), 371 (7.27); pmr (DMSO-d$_6$), δ 0.8–2.0 (m, 10, cyclohexane CH$_2$), 2.40 (m, 1, NCH), 3.88 (s, 2, CH$_2$N), 6.52 (s, 2, NH$_2$), 7.59 (s, 2, NH$_2$), 8.74 (s, 1, C$_7$—H).

EXAMPLE 27

Diethyl N-[α-(2,4-diamino-6-pteridinyl)-4-anisoyl]-L-glutamate (27) Hemihydrate

A mixture of NaH (0.30 g of 50% dispersion in oil, 6.2 mmoles) and diethyl N-(4-hydroxybenzoyl)-L-glutamate (2.00 g, 6.20 mmoles) in DMAC (25 ml) was stirred under N$_2$ with ice-bath cooling until solution was complete and H$_2$ evolution had ceased. Solid I (1.04 g, 3.10 mmoles) was then added. The resulting dark-red solution was kept at about 25° under N$_2$ in a stoppered flask protected from light for 8 days. Addition to dilute HCl solution (150 ml of 0.01 N) gave an orange solid, which was collected by filtration, washed with H$_2$O followed by Et$_2$O, and dried in vacuo (25°, P$_2$O$_5$); yield 70% (1.08 g). This material, which was used without further purification for conversion to 28, gave a well-resolved pmr spectrum consistent with the assigned structure. The only extraneous signal was that due to H$_2$O of hydration; pmr (DMSO-d$_6$), δ 1.20 (m, 6, CH$_3$), 2.08 (m, 2, CHCH$_2$CH$_2$), 2.40 (m, 2, CH$_2$CH$_2$CO), 3.46 (broad s, 2, H$_2$O), 4.10 (m, 4, OCH$_2$CH$_3$), 4.44 (m, 1, NHCHCH$_2$), 5.30 (s, 2, CH$_2$OC$_6$H$_4$), 6.74 (s, 2, NH$_2$), 7.16 and 7.90 (m, 4, C$_6$H$_4$), 7.70 (broad s, 2, NH$_2$), 8.58 (d, 1, NHCH), 8.87 (s, 1, C$_7$—H). The ir spectrum of the sample described is identical with that of a sample obtained from a trial run that gave the following elemental analysis results. Anal. Calcd for C$_{23}$H$_{27}$—N$_7$O$_6$.0.5H$_2$O: C, 54.54; H, 5.57; N, 19.36. Found: C, 54.81; H, 5.77; N, 19.19.

EXAMPLE 28

N-[α-(2,4-diamino-6-pteridinyl)-4-anisoyl]-L-glutamic Acid (28) Monohydrate

The diethyl ester 27 (1.00 g) was dissolved with stirring in warm DMAC (15 ml). The dark-orange solution was cooled to 25°, and NaOH solution (40 ml of 0.1 N) was added in a thin stream. Cloudiness developed initially but soon cleared, and the solution was kept at 20°-25° under $N_2$ in a stoppered flask protected from light for 19 hrs. The solution was treated with Norit and filtered (Celite) to give a yellow-orange filtrate of pH 8.2. Careful treatment with 1 N HCl to produce pH 3.0 gave a yellow precipitate. After refrigeration (3 hrs.), the mixture was centrifuged, and the solid residue was washed twice with $H_2O$ (30-ml portions) with centrifugation followed by decantation. The solid was again suspended in $H_2O$, collected by filtration, and dried in vacuo (25° over $P_2O_5$ and NaOH pellets); yield 0.73 g. This sample produced a thin-layer chromatogram that revealed one migrating spot that fluoresced under uv light. A pale fluorescing spot remained at the origin. The sample was suspended in $H_2O$ (5 ml) and treated with NaOH solution (11 ml of 0.3 N) to redissolve. Clarification (Norit, Celite) was followed by addition of dilute HCl to pH 3.0. The precipitate was isolated as before and found by tlc to be homogeneous; yield 72% (0.65 g). Anal. Calcd for $C_{19}H_{19}N_7O_6 \cdot H_2O$: C, 49.67; H, 4.61; N, 21.34. Found: C, 49.27; H, 4.23; N, 21.52. Spectral data: $\lambda_{max}$, nm ($\epsilon \times 10^{-3}$), 0.1 N HCl, 248 (32.2), 336 (11.2), 348 (sh) (10.0); pH 7, 260 (39.6), 370 (7.90); 0.1 N NaOH, 260 (40.0) 370 (8.21); pmr ($CF_3CO_2D$), δ 2.54 (m, 2, $CHCH_2CH_2$), 2.83 (m, 2, $CH_2CO_2H$), 5.12 (m, 1, $CHCO_2H$), 5.54 (s, 2, $CH_2OC_6H_4$), 7.24 and 7.94 (m, 4, $C_6H_4$), 9.22 (s, 1, $C_7$—H).

EXAMPLE 29

α-(2,4-Diamino-6-pteridinyl)-4-anisamide (29) Hemihydrate

Solid NaH (127 mg of 57% dispersion in mineral oil, 3.0 mmoles) was added to a solution of 4-hydroxybenzamide (412 mg, 3.00 mmoles) in DMAC (15 ml). When the evolution of $H_2$ was complete, solid I (504 mg, 1.50 mmoles) was added with stirring. After 141 hrs at about 25°, the reaction mixture was diluted with $H_2O$ (200 ml); the precipitate was collected by filtration, washed with petroleum ether and dried in vacuo (78°, $P_2O_5$); yield 61% (293 mg), mp > 325° (Mel-Temp). This sample was homogeneous by tlc ($CHCl_3$—MeOH, 5:1). Anal. Calcd for $C_{14}H_{13}N_7O_2 \cdot 0.5H_2O$: C, 52.51; H, 4.41; N, 30.61. Found: C, 52.41; H, 4.49; N, 30.87. Spectral data: $\lambda_{max}$, nm ($\epsilon \times 10^{-3}$), 0.1 N HCl, 248 (25.8), 337 (10.3), 347 (sh) (9.37); pH 7, 260 (29.6), 371 (6.91); 0.1 N NaOH, 260 (30.0), 372 (7.55); pmr (DMSO-$d_6$), δ 3.36 ($NH_2$ and $H_2O$), 5.28 (s, $CH_2O$), 6.72 and 7.68 ($NH_2$), 7.50 (m, 4, $C_6H_4$), 8.86 (s, 1, $C_7$—H).

EXAMPLE 30

6-[(Phenoxy)methyl]-2,4-pteridinediamine (30)

Treatment of phenol with NaH followed by I in DMAC as described for 29 led to 30, mp about 285° dec (Mel-Temp), in 70% yield (283 mg from 1.50 mmoles of I) after a 72 hr reaction period. (The isolation procedure was the same as that given for 29.) The sample was homogeneous by tlc ($CHCl_3$—MeOH, 5:1) except for a faint shadow near the origin. Anal. Calcd for $C_{13}H_{12}N_6O$: C, 58.20; H, 4.51; N, 31.33. Found: C, 57.93; H, 4.26; N, 31.58. Spectral data: $\lambda_{max}$, nm ($\epsilon \times 10^{-3}$), 0.1 N HCl, 244 (17.7), 276 (5.26), 287 (5.32), 337 (10.4), 347 (sh) (9.35); pH 7, 260 (24.9), 372 (7.44); 0.1 N NaOH, 260 (25.1), 372 (7.58); pmr (DMSO-$d_6$), δ 5.22 (s, 2, $CH_2O$), 6.69 (s, 2, $NH_2$), 7.64 (s, 2, $NH_2$), 7.15 (m, 5, $C_6H_5$), 8.83 (s, 1, $C_7$—H).

EXAMPLE 31

6-[(Phenylthio)methyl]-2,4-pteridinediamine (31) Hemihydrate

Solid I (1.50 mmoles) was added to a stirred, externally cooled (ice bath) mixture of anhydrous $K_2CO_3$ (221 mg, 1.60 mmoles) and thiophenol (0.5 ml, approximately 5 mmoles) in DMAC (5 ml). The mixture was stirred at 20°-25° for 21 hrs. The yellow precipitate was collected, washed successively with $Et_2O$ and $H_2O$, and dried in vacuo (78°, $P_2O_5$); yield 87% (370 mg), mp 270°-272° dec (Mel-Temp). The product was homogeneous by tlc ($CHCl_3$—MeOH, 5:1), Anal. Calcd for $C_{13}H_{12}N_6S \cdot 0.5H_2O$: C, 53.23; H, 4.47; N, 28.65. Found: C, 53.10; H, 4.09; N, 28.79. Spectral data: $\lambda_{max}$, nm ($\epsilon \times 10^{-3}$), 0.1 N HCl, 247 (22.7), 342 (9.75); pH 7, 260 (26.4), 285 (sh) (8.90), 375 (8.07); 0.1 N NaOH, 260 (26.9), 286 (sh) (9.05), 376 (8.22); pmr (DMSO-$d_6$), δ 4.39 (s, 2, $CH_2S$), 6.64 (s, 2, $NH_2$), 7.42 (m, 7, $C_6H_5$ and $NH_2$), 8.67 (s, 1, $C_7$—H).

It is noted that all temperatures given herein are in degrees centigrade.

It should now be apparent that the objects initially set forth have been successfully achieved. Moreover, while there is shown and described present preferred embodiments of the invention, it is to be distinctly understood that the invention is not limited thereto, but may be otherwise variously embodied and practiced within the scope of the following claims.

Accordingly, what is claimed is:

1. A method of making 6-(bromomethyl)-2,4-diaminopteridine hydrobromide comprising reacting 2,4-diamino-6-pteridinemethanol.HBr with triphenylphosphine dibromide in a reaction medium of N,N-dimethylacetamide.

2. A method of making 6-(bromomethyl)-2,4-diaminopteridine hydrobromide comprising reacting 2,4-diamino-6-pteridinemethanol.HBr with phosphorus tribromide in a reaction medium of N,N-dimethylformamide.

3. A method of making pteridine compounds represented by the formula:

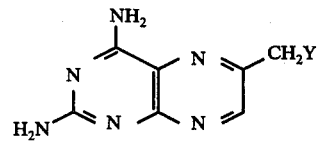

wherein
Y is a member selected from the group consisting of —NRR$^1$R$^2$, —NH(CH$_2$)$_2$C$_6$H$_5$,

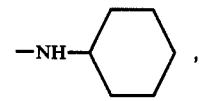

—OR$^3$, and —SC$_6$H$_5$;
R is H or CH$_3$;

$R^1$ is —$C_6H_4R^4$,

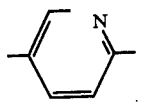

or —$(CH_2)_m$—;
$R^2$ is —H, —CONHCH(COOR$^5$)(CH$_2$)$_n$ COOR$^5$, —CONHCH$_2$COOH, —COOH, —CONH$_2$, —CONH(CH$_2$)$_2$CH$_3$, —CON(CH$_3$)$_2$, —COCH$_3$, —NHCOCH$_3$, —CONH(CH$_2$)$_3$CO$_2$H, —(CH$_2$)$_2$NHCOCH$_3$, —OCH$_3$, —Cl, or —O(CH$_2$)$_2$OCH$_2$CH$_3$;
$R^3$ is $C_6H_4R^6$;
$R^4$ is (CH$_2$)$_p$ or (SO$_2$)$_q$;
$R^5$ is —H or -CH$_3$;
$R^6$ is —H, —CONHCH(COOC$_2$H$_5$)(CH$_2$)$_2$COOC$_2$H$_5$, —CONHCH(COOH)(CH$_2$)$_2$COOH, or —CONH$_2$;
m is 2, 3 or 4; n is 1 or 2; p is 0, 1 or 2; and q is 0 or 1
comprising reacting 6-(bromomethyl)-2,4-diaminopteridine hydrobromide with a compound represented by the formula HY, where Y is as defined above, in a reaction medium of N,N-dimethylacetamide or N,N-dimethylformamide and recovering said pteridine compound.

4. The method as defined in claim 3, wherein said 6-(bromomethyl)-2,4-diaminopteridine is reacted with said HY in the absence of light.

5. The method as defined in claim 3, wherein the molar ratio of said 6-(bromomethyl)-2,4-diaminopteridine and said HY is from 1:1 to 1:4.

6. A method of making methotrexate as defined in claim 3, wherein Y is —N(CH$_3$)C$_6$H$_4$CONHCH(COOH)(CH$_2$)$_2$COOH.

7. A method of making aminopterine as defined in claim 3, wherein Y is —NHC$_6$H$_4$CONHCH(COOH)(CH$_2$)$_2$COOH.

8. A method of making pteridine compounds represented by the formula:

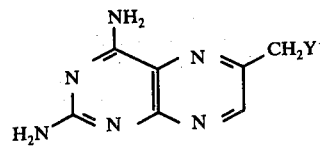

wherein
Y is a member selected from the group consisting of —NRR$^1$R$^2$, —NH(CH$_2$)$_2$C$_6$H$_5$,

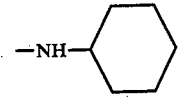

—OR$^3$, and —SC$_6$H$_5$;
R is H or CH$_3$;
$R^1$ is —C$_6$H$_4$R$^4$,

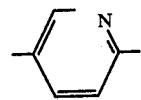

or —(CH$_2$)$_m$—;
$R^2$ is —H, —CONHCH(COOR$^5$)(CH$_2$)$_n$ COOR$^5$, —CONHCH$_2$COOH, —COOH, —CONH$_2$, —CONH(CH$_2$)$_2$CH$_3$, —CON(CH$_3$)$_2$, —COCH$_3$, —NHCOCH$_3$, —CONH(CH$_2$)$_3$CO$_2$H, —(CH$_2$)$_2$NHCOCH$_3$, —OCH$_3$, —Cl, or —O(CH$_2$)$_2$OCH$_2$CH$_3$;
$R^3$ is C$_6$H$_4$R$^6$;
$R^4$ is (CH$_2$)$_p$ or (SO$_2$)$_q$;
$R^5$ is —H or —CH$_3$;
$R^6$ is —H, —CONHCH(COOC$_2$H$_5$)(CH$_2$)$_2$COOC$_2$H$_5$, —CONHCH(COOH)(CH$_2$)$_2$COOH, or —CONH$_2$;
m is 2, 3 or 4; n is 1 or 2; p is 0, 1 or 2; and q is 0 or 1
comprising reacting 2,4-diamino-6-pteridinemethanol.HBr with triphenylphosphine dibromide in a reaction medium of N,N-dimethylacetamide or with phosphorus tribromide in a reaction medium of N,N-dimethylformamide to form 6-(bromomethyl)-2,4-diaminopteridine hydrobromide, reacting said 6-(bromomethyl)-2,4-diaminopteridine hydrobromide with a compound represented by the formula HY, where Y is as defined above, and recovering said pteridine compound.

* * * * *